(12) United States Patent
Ellers-Lenz et al.

(10) Patent No.: US 8,877,814 B2
(45) Date of Patent: Nov. 4, 2014

(54) TITRATION PACKAGE FOR NERAMEXANE AND ITS USE IN THE TREATMENT OF AN INNER EAR DISORDER

(75) Inventors: Barbara Ellers-Lenz, Morfelden-Walldorf (DE); Tanja Rosenberg, Hamburg (DE); Erhard Seiller, Nidderau (DE); Hagen Kruger, Frankfurt am Main (DE); Michael Althaus, Schoeneck (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 142 days.

(21) Appl. No.: 12/733,645

(22) PCT Filed: Sep. 10, 2008

(86) PCT No.: PCT/EP2008/007420
§ 371 (c)(1),
(2), (4) Date: Jul. 28, 2010

(87) PCT Pub. No.: WO2009/033651
PCT Pub. Date: Mar. 19, 2009

(65) Prior Publication Data
US 2010/0298441 A1 Nov. 25, 2010

Related U.S. Application Data

(60) Provisional application No. 60/993,396, filed on Sep. 12, 2007, provisional application No. 61/066,931, filed on Feb. 25, 2008, provisional application No. 61/067,026, filed on Feb. 25, 2008, provisional application No. 61/067,083, filed on Feb. 25, 2008.

(30) Foreign Application Priority Data

| Sep. 12, 2007 | (EP) | 07253630 |
|---|---|---|
| Mar. 14, 2008 | (EP) | 08004776 |
| Mar. 14, 2008 | (EP) | 08004777 |
| Mar. 14, 2008 | (EP) | 08004778 |

(51) Int. Cl.
*A61K 31/13* (2006.01)
*A61P 27/16* (2006.01)
*C07C 211/35* (2006.01)
*A61K 9/20* (2006.01)

(52) U.S. Cl.
CPC .............. *A61K 31/13* (2013.01); *A61K 9/2054* (2013.01)
USPC .......................................... 514/579; 564/462

(58) Field of Classification Search
CPC ................................ A61K 31/13; C07C 211/35
USPC ........................... 517/579; 514/579; 564/462
See application file for complete search history.

(56) References Cited

U.S. PATENT DOCUMENTS

| 6,034,134 A | 3/2000 | Gold et al. |
|---|---|---|
| 6,066,652 A * | 5/2000 | Zenner et al. ................ 514/317 |
| 6,071,966 A | 6/2000 | Gold |
| 2003/0236286 A1 | 12/2003 | Deorazio et al. |
| 2006/0002999 A1 * | 1/2006 | Yang et al. .................... 424/464 |
| 2006/0264897 A1 * | 11/2006 | Lobl et al. ..................... 604/506 |
| 2007/0141148 A1 * | 6/2007 | Hauptmeier et al. ......... 424/468 |

FOREIGN PATENT DOCUMENTS

| WO | WO 98/10757 | 3/1998 |
|---|---|---|
| WO | WO 2004/043899 | 5/2004 |
| WO | WO 2005009326 | 2/2005 |
| WO | WO 2005044228 | 5/2005 |
| WO | WO 2006069294 | 6/2006 |
| WO | WO 2006/079055 | 7/2006 |
| WO | WO 2006096194 | 9/2006 |
| WO | WO 2007/062815 | 6/2007 |
| WO | WO 2007062815 | 6/2007 |

OTHER PUBLICATIONS

European Search Report for 08004778 of Aug. 13, 2008.
International Search Report and Written Opinion for PCT/EP2008/007420 of Jan. 16, 2009.
P. Plazas, et al., "Inhibition of the Alpha9Alpha10 nicotinic cholinergic receptor by neramexane, an open channel blocker of N-methyl-D-aspartate receptors" European Journal of Pharmacology vol. 566, p. 11-19, 2007.
Basile, et al., Nature Medicine, 1996, 2, 1338-1343.
Duan, et al., PNAS, 2000, 97, 7597-7602.
Eggermont, et al., Drug Discovery Today, 2005, 10, 1283-1290.
European Search Report for European Application No. 07253630.3 of Dec. 6, 2007.
European Search Report for European Application No. 08004776.4 of May 21, 2008.
European Search Report for European Application No. 08004777.2 of Jul. 2, 2008.

* cited by examiner

*Primary Examiner* — Kendra D Carter
*Assistant Examiner* — Jason A Deck
(74) *Attorney, Agent, or Firm* — Hueschen and Sage

(57) ABSTRACT

The present invention relates to a titration scheme for the administration of a 1-amino-alkylcyclohexane derivative which allows for quick attainment of an effective dose of a 1-amino-alkylcyclohexane derivative while minimizing side effects. The present invention further relates to a titration package for providing a 1-amino-alkylcyclohexane derivative (e.g., neramexane or a pharmaceutically acceptable salt thereof) in at least two different dosages. The present titration scheme/titration package may be useful in the treatment of various diseases, including tinnitus.

8 Claims, 7 Drawing Sheets

TITRATION PACKAGE FOR NERAMEXANE AND ITS USE IN THE TREATMENT OF AN INNER EAR DISORDER

FIELD OF THE INVENTION

The present invention relates to a titration scheme for the administration of a 1-amino-alkylcyclohexane derivative which allows for quick and safe attainment of an effective dose of a 1-amino-alkylcyclohexane derivative while minimizing side effects. The present intervention further relates to a titration scheme allowing for a quick and safe uptitration to at least two different and weight-adapted maintenance dosages. The present invention further relates to a titration package for providing a 1-amino-alkylcyclohexane derivative (e.g., neramexane or a pharmaceutically acceptable salt thereof) in at least two different dosages. The present titration scheme/titration package is expected be useful in the treatment of various inner ear disorders, including tinnitus.

BACKGROUND OF THE INVENTION

Inner ear disorders are an increasing problem in nowadays society. The most common of these disorders, tinnitus is commonly referred to as 'ringing in the ears'—the perception of sounds in the absence of an external source of acoustic signals. Tinnitus has been defined as "the perception of a sound which results exclusively from the activity within the nervous system without any corresponding mechanical, vibratory activity within the cochlea, that is, tinnitus as an auditory phantom perception" (Jastreboff et al., J Am Acad Audiol 2000; 11(3): 162-177). For the individual patient, tinnitus may be tolerable or it may represent a debilitating illness preventing its sufferers from sleep or work. Tinnitus is frequently associated with a decreased sound tolerance (i.e. hyperacusis).

The pathophysiology of subjective tinnitus is poorly understood and a definitive pathogenesis of tinnitus is unknown. Many environmental and substance-induced factors may cause tinnitus. Among the most frequently cited factors are acute acoustic trauma, occupational noise, and recreational music. In general, tinnitus seems to be the result of neuronal dysfunction within the auditory pathway. This dysfunction is misleadingly perceived as sound by higher auditory centers and can lead to functional alterations within the auditory nervous system. Maladaptive functional changes in cortical structures could result in an altered balance between excitatory and inhibitory neurotransmission and may lead to more severe tinnitus. In all cases, a potential malfunction in auditory pathways and auditory cortex is related to the activity of the prefrontal cortex and limbic system.

In most cases (95%), the perceived tinnitus is purely subjective in nature, e.g. no physical source of acoustic signals can be identified and, therefore, cannot be heard externally. A physical examination is performed to exclude objective tinnitus, e.g. the patient's perception of sound is caused by a real source of sound waves, e.g. the sound from turbulent flow in blood vessels reaching the cochlea. Tinnitus may be classified according to duration of tinnitus and the degree of tinnitus expression (e.g. severity or annoyance of the tinnitus) (McCombe et al., Clin Otolaryngol 2001; 26(5): 388-393 and Davis et al., Epidemiology of Tinnitus. In: Tyler R, editor. Tinnitus Handbook. San Diego: Singular Publishing Group; 2000. p. 1-23). Regarding the impact of tinnitus, tinnitus may be severely annoying to the patient and can be accompanied by social and psychological complications.

There are currently no well-established, specific medical treatments for tinnitus that provide replicable reduction of tinnitus and annoyance due to tinnitus, in excess of placebo effects (Dobie, Laryngoscope 1999; 109(8): 1202-1211; Eggermont et al., Trends Neurosci 2004; 27(11): 676-682; and Patterson et al., Int Tinnitus J 2006; 12(2): 149-159).

1-Amino-alkylcyclohexanes such as neramexane (also known as 1-amino-1,3,3,5,5-pentamethylcyclohexane) have been found to be useful in the therapy of various diseases especially in certain neurological diseases, including Alzheimer's disease and neuropathic pain. 1-Amino-alkylcyclohexanes such as neramexane are disclosed, for example, in detail in U.S. Pat. Nos. 6,034,134 and 6,071,966. Insofar as the chemical variations of 1-aminoaklylcyclohexanes are concerned, the respective subject matter of these patents is hereby incorporated by reference. It is believed that the therapeutic action of 1-amino-alkylcyclohexanes such as neramexane is related to the inhibition of the effects of excessive glutamate at the N-methyl-D-aspartate (NMDA) receptors of nerve cells, for which reason the compounds are also categorized as n NMDA antagonists, or NMDA receptor antagonists. Neramexane has also been disclosed to exhibit activity at the $\alpha$ 9/$\alpha$ 10 nicotinic (Plazas, et al., Eur J. Pharmacol., 2007 Jul. 2; 566(1-3):11-19) and 5-HT$_3$ receptors).

Drug-related adverse events may be avoided or minimized by using a suitable up-titration period. Thus, a need exists for a suitable titration scheme which allows an effective dose to be quickly achieved while minimizing side effects. Moreover, a need also exists for a titration package which allows for compliance with a regimen of changing dosage of 1-amino-alkylcyclohexane derivatives over time. Such titration packages are also known as "compliance packages" as they aid the patient in complying with the therapeutically indicated dosage regime.

The present inventors have found that neramexane may be useful in treating tinnitus. The present inventors have also developed a titration scheme for the administration of a 1-amino-alkylcyclohexane derivative which allows for quick attainment of an effective dose of a composition comprising a 1-amino-alkylcyclohexane derivative while minimizing side effects. Moreover, the present inventors have developed a titration scheme allowing for a quick and safe up titration to at least two different and weight-adapted maintenance dosages. Moreover, the present inventors have developed a titration package comprising at least two different dosages of a 1-amino-alkylcyclohexane derivative, e.g. neramexane which allows for a suitable up-titration period to produce an acceptable number of occurrences of drug-related adverse events. Such a titration scheme/package may be suitable for use in the treatment of tinnitus.

SUMMARY OF THE INVENTION

The present invention relates to a 1-amino-alkylcyclohexane derivative (e.g., neramexane or a pharmaceutically acceptable salt thereof such as neramexane mesylate) for the treatment of an inner ear disorder, e.g. tinnitus, wherein said derivative is administered in a titration scheme. Said titration scheme provides quick and safe attainment of an effective dose. By this kind of administration, side effects attributed to the administration of 1-amino-alkylcyclohexane derivatives are minimized.

A further aspect of the invention relates to the use of a 1-amino-alkylcyclohexane derivative (e.g., neramexane or a pharmaceutically acceptable salt thereof such as neramexane mesylate) for the manufacture of a medicament for the treatment of an inner ear disorder, e.g. tinnitus, wherein said medicament is administered in a titration scheme which provides quick and safe attainment of an effective dose. By this kind of administration, side effects attributed to the administration of 1-amino-alkylcyclohexane derivatives are minimized. The medicament specified herein is for the administration according to the titration scheme disclosed herein.

The 1-amino-alkylcyclohexane derivative as well as the medicament specified herein are for the administration according to the above administration scheme. In one embodiment the derivative/medicament is specifically adapted to provide the respective information regarding the titration scheme to the patient. The respective information regarding the specific titration scheme may be provided via e.g. the respective information in or on the package, the dosage form and/or the package leaflet and/or the patient information. The respective information regarding the specific administration scheme can be provided via e.g. the respective information in or on the package, and/or the package leaflet, and/or the patient information, as well as the appearance of the dosage forms provided, e.g. tablet form or tablet color.

A further aspect of the invention relates to the derivative/use specified above wherein said titration scheme comprises up-titration of a 1-amino-alkylcyclohexane derivative (e.g., neramexane or a pharmaceutically acceptable salt thereof such as neramexane mesylate) over a period of from four to five weeks to achieve an effective dose.

In a further aspect of the invention the titration scheme comprises up-titration of a 1-amino-alkylcyclohexane derivative (e.g., neramexane or a pharmaceutically acceptable salt thereof such as neramexane mesylate) over a period of from four to five weeks to achieve an effective dose of from 5 to 150 mg per day.

In a further aspect of the invention the titration scheme comprises up-titration of a 1-amino-alkylcyclohexane derivative (e.g., neramexane or a pharmaceutically acceptable salt thereof such as neramexane mesylate) over a period of from four to five weeks to achieve an effective dose of from 50 to 75 mg per day.

In a further aspect of the invention the titration scheme comprises up-titration of a 1-amino-alkylcyclohexane derivative in increasing dosages of 25 mg or 12.5 mg steps at weekly intervals.

In a further aspect of the invention the 1-amino-cyclohexane is neramexane or a pharmaceutically acceptable salt thereof, e.g. neramexane mesylate.

In a further aspect of the invention the titration scheme comprises up-titration of neramexane, or a pharmaceutically acceptable salt thereof (e.g., neramexane mesylate), over a period of four weeks to achieve an effective dose of 50 mg per day while minimizing side effects.

In a further aspect of the invention neramexane or a pharmaceutically acceptable salt thereof (e.g., neramexane mesylate) is administered according to the following schedule: once daily at a dose of 12.5 mg per day for the first week, twice daily, wherein each dose is 12.5 mg for the second week, twice daily, wherein one dose is 12.5 mg and the other dose is 25 mg for the third week, and twice daily, wherein each dose is 25 mg for the fourth week.

In a further aspect of the invention neramexane mesylate is administered according to such schedule. If another pharmaceutically acceptable salt, a solvate, an isomer, a conjugate, a prodrug or a derivative thereof, such as neramexane hydrochloride, is administered, equimolar amounts of another pharmaceutically acceptable salt, a solvate, an isomer, a conjugate, a prodrug or a derivative thereof, such as neramexane hydrochloride, may also be used.

In a further aspect of the invention neramexane or a pharmaceutically acceptable salt thereof (e.g., neramexane mesylate) is administered according to the following schedule: once daily at a dose of 12.5 mg per day for the first week, twice daily, wherein each dose is 12.5 mg for the second week, twice daily, wherein one dose is 12.5 mg and the other dose is 25 mg for the third week, and twice daily, wherein each dose is 25 mg for the fourth week, wherein, in weeks during which mixed doses are administered, the dose comprising the higher concentration is administered in the second daily dose.

In a further aspect of the invention neramexane mesylate is administered according to such schedule. If another pharmaceutically acceptable salt, a solvate, an isomer, a conjugate, a prodrug or a derivative thereof, such as neramexane hydrochloride, is administered, equimolar amounts of another pharmaceutically acceptable salt, a solvate, an isomer, a conjugate, a prodrug or a derivative thereof, such as neramexane hydrochloride, may also be suitable.

In a further aspect of the invention the titration scheme comprises treatment with neramexane, or a pharmaceutically acceptable salt thereof (e.g., neramexane mesylate), which titration scheme allows for up-titration of neramexane, or a pharmaceutically acceptable salt thereof (e.g., neramexane mesylate), over a period of five weeks to achieve an effective dose of 75 mg per day while minimizing side effects.

In a further aspect of the invention neramexane or a pharmaceutically acceptable salt thereof (e.g., neramexane mesylate) is administered according to the following schedule: once daily at a dose of 12.5 mg per day for the first week, twice daily, wherein each dose is 12.5 mg for the second week, twice daily, wherein one dose is 12.5 mg and the other dose is 25 mg for the third week, and twice daily, wherein each dose is 25 mg for the fourth week, and twice daily, wherein each dose is 37.5 mg for the fifth week.

In a further aspect of the invention neramexane mesylate is administered according to such schedule. If another pharmaceutically acceptable salt, a solvate, an isomer, a conjugate, a prodrug or a derivative thereof, such as neramexane hydrochloride, is administered, equimolar amounts of another pharmaceutically acceptable salt, a solvate, an isomer, a conjugate, a prodrug or a derivative thereof, such as neramexane hydrochloride, may also be used.

In a further aspect of the invention neramexane or a pharmaceutically acceptable salt thereof (e.g., neramexane mesylate) is administered according to the following schedule: once daily at a dose of 12.5 mg per day for the first week, twice daily, wherein each dose is 12.5 mg for the second week, twice daily, wherein one dose is 12.5 mg and the other dose is 25 mg for the third week, and twice daily, wherein each dose is 25 mg for the fourth week, and twice daily, wherein each dose is 37.5 mg for the fifth week, wherein, in weeks during which mixed doses are administered, the dose comprising the higher concentration is administered in the second daily dose.

In a further aspect of the invention neramexane mesylate is administered according to such schedule. If another pharmaceutically acceptable salt, a solvate, an isomer, a conjugate, a prodrug or a derivative thereof, such as neramexane hydrochloride, is administered, equimolar amounts of another pharmaceutically acceptable salt, a solvate, an isomer, a conjugate, a prodrug or a derivative thereof, such as neramexane hydrochloride, may also be suitable.

In a further aspect of the invention neramexane or a pharmaceutically acceptable salt (e.g., neramexane mesylate) thereof is administered according to the following schedule: once daily at a dose of 25 mg per day for the first week, once daily at a dose of 50 mg per day for the second week, and, optionally, once daily at a dose of 75 mg per day for the third week.

In a further aspect of the invention neramexane or a pharmaceutically acceptable salt thereof (e.g., neramexane mesylate) is administered in the form of a modified release once daily formulation according to the following schedule: once daily at a dose of 12.5 mg for the first week, once daily at a dose of 25 mg for the second week, once daily at a dose of 37.5 mg for the third week, once daily at a dose of 50 mg for the fourth week, for subjects with a weight up to 90 kg, and—in addition to the above—once daily a dose of 75 mg for subjects having a weight of more than 90 kg.

A further aspect of the invention relates to such a titration scheme, wherein neramexane mesylate is administered according to such schedule. If another pharmaceutically acceptable salt, a solvate, an isomer, a conjugate, a prodrug or a derivative thereof, such as neramexane hydrochloride, is administered, equimolar amounts of another pharmaceutically acceptable salt, a solvate, an isomer, a conjugate, a prodrug or a derivative thereof, such as neramexane hydrochloride, may also be suitable.

In a further aspect of the invention the composition comprising neramexane or a pharmaceutically acceptable salt thereof (e.g., neramexane mesylate) is administered in the form of a modified release once daily formulation according to the following schedule: once daily at a dose of 25 mg for the first week, once daily at a dose of 50 mg for the second week, for subjects with a weight up to 90 kg, and—in addition to the above—once daily a dose of 75 mg for subjects having a weight of more than 90 kg.

A further aspect of the invention relates to such a titration scheme, wherein neramexane mesylate is administered according to such schedule. If another pharmaceutically acceptable salt, a solvate, an isomer, a conjugate, a prodrug or a derivative thereof, such as neramexane hydrochloride, is administered, equimolar amounts of another pharmaceutically acceptable salt, a solvate, an isomer, a conjugate, a prodrug or a derivative thereof, such as neramexane hydrochloride, may also be suitable.

In a further aspect of the invention the inner ear disorder is at least one selected among tinnitus, vertigo, such as paroxymal position vertigo (BPPV), hearing loss, chronic ear pain, perilymphatic fistula, secondary endolymphatic hydrops, labyrinthitis and vestibular neuritis, acoustic neurome, otootxicity, autoimmune inner ear dieses (AIED) and Meniere's disease.

The present invention further relates to a titration scheme for treatment of an inner ear disorder (e.g., tinnitus) which provides quick attainment of an effective dose of a composition comprising a 1-amino-alkylcyclohexane derivative (e.g., neramexane or a pharmaceutically acceptable salt thereof, such as neramexane mesylate) while minimizing side effects.

A further aspect of the invention relates to such a titration scheme which comprises up-titration of a composition comprising a 1-amino-alkylcyclohexane derivative (e.g., neramexane or a pharmaceutically acceptable salt thereof, such as neramexane mesylate) over a period of from four to five weeks to achieve an effective dose while minimizing side effects.

A further aspect of the invention relates to such a titration scheme which comprises up-titration of a composition comprising a 1-amino-alkylcyclohexane derivative (e.g., neramexane or a pharmaceutically acceptable salt thereof, such as neramexane mesylate) over a period of from four to five weeks to achieve an effective dose of from 5 to 150 mg per day while minimizing side effects.

A further aspect of the invention relates to such a titration scheme which comprises up-titration of a composition comprising a 1-amino-alkylcyclohexane derivative (e.g., neramexane or a pharmaceutically acceptable salt thereof, such as neramexane mesylate) over a period of from four to five weeks to achieve an effective dose of from 50 to 75 mg per day while minimizing side effects.

A further aspect of the invention relates to such a titration scheme wherein the titration scheme comprises treatment with a composition comprising neramexane or a pharmaceutically acceptable salt thereof (e.g., neramexane mesylate) and which titration scheme comprises up-titration of a composition comprising neramexane, or a pharmaceutically acceptable salt thereof, over a period of four weeks to achieve an effective dose of 50 mg per day while minimizing side effects.

A further aspect of the invention relates to such a titration scheme wherein the composition comprising neramexane or a pharmaceutically acceptable salt thereof (e.g., neramexane mesylate) is administered according to the following schedule: once daily at a dose of 12.5 mg per day for the first week, twice daily, wherein each dose is 12.5 mg for the second week, twice daily, wherein one dose is 12.5 mg and the other dose is 25 mg for the third week, and twice daily, wherein each dose is 25 mg for the fourth week.

A further aspect of the invention relates to such a titration scheme wherein in weeks during which mixed doses are administered, the dose comprising the higher concentration is administered in the second daily dose.

A further aspect of the invention relates to such a titration scheme wherein the titration scheme comprises treatment with a composition comprising neramexane or a pharmaceutically acceptable salt thereof (e.g., neramexane mesylate) and which titration scheme comprises up-titration of a composition comprising neramexane, or a pharmaceutically acceptable salt thereof, over a period of five weeks to achieve an effective dose of 75 mg per day while minimizing side effects.

A further aspect of the invention relates to such a titration scheme wherein the composition comprising neramexane or a pharmaceutically acceptable salt thereof (e.g., neramexane mesylate) is administered according to the following schedule: once daily at a dose of 12.5 mg per day for the first week, twice daily, wherein each dose is 12.5 mg for the second week, twice daily, wherein one dose is 12.5 mg and the other dose is 25 mg for the third week, and twice daily, wherein each dose is 25 mg for the fourth week, and twice daily, wherein each dose is 37.5 mg for the fifth week.

A further aspect of the invention relates to such a titration scheme wherein in weeks during which mixed doses are administered, the dose comprising the higher concentration is administered in the second daily dose.

The present invention further relates to a titration scheme for treatment of a 1-amino-alkylcyclohexane derivative responsive condition which provides quick attainment of an effective dose of a composition comprising a 1-amino-alkylcyclohexane derivative (e.g., neramexane or a pharmaceutically acceptable salt thereof, such as neramexane mesylate) while minimizing side effects.

The present invention further relates to a titration package for providing a 1-amino-alkylcyclohexane derivative (e.g., neramexane or a pharmaceutically acceptable salt thereof such as neramexane mesylate), wherein the 1-amino-alkylcyclohexane derivative is present, e.g. in at least two different dosages. Said titration package may be used in the treatment of inner ear diseases according to the titration scheme disclosed therein.

A further aspect of the invention relates to a titration package for providing a 1-amino-alkylcyclohexane derivative (e.g., neramexane or a pharmaceutically acceptable salt thereof such as neramexane mesylate) in at least two different dosages wherein the titration package comprises at least two sets of dosage forms of like dosage, each set comprises at least three individually addressable regions, and each addressable region comprises or is represented by a 1-amino-alkylcyclohexane derivative (e.g., neramexane or a pharmaceutically acceptable salt thereof such as neramexane mesylate), including a tablet.

A further aspect of the invention relates to a titration package for providing a pharmaceutical composition comprising a 1-amino-alkylcyclohexane derivative (e.g., neramexane or a pharmaceutically acceptable salt thereof such as neramexane mesylate) in at least two different dosages wherein the titration package comprises at least two sets of dosage forms of like dosage, each set comprises at least three individually addressable regions, and each addressable region comprises or is represented by a pharmaceutical composition, including a tablet.

A further aspect of the invention relates to such a titration package wherein the at least three individually addressable regions within each set are arranged essentially along at least one horizontal line (defining a "row") or are arranged essentially along at least one vertical line (defining a "column").

An additional embodiment of the invention relates to such a titration package wherein the at least three addressable regions of the at least two sets of dosage forms of like dosage are differentiated from each other by at least one means selected from the following group, or any combination thereof: highlighting by color and/or shading and/or imprint, provision of a blister pack at the position of the addressable region; provision of an indentation/elevation; provision of a different material or a gradient in material, provision of a pouch or a blister or other conceivable containment for the 1-amino-alkylcyclohexane derivative (e.g, neramexane or a pharmaceutically acceptable salt thereof such as neramexane mesylate).

An additional embodiment of the invention relates to such a titration package wherein the 1-amino-alkylcyclohexane derivative (e.g, neramexane or a pharmaceutically acceptable salt thereof such as neramexane mesylate) is a solid.

An additional embodiment of the invention relates to such a titration package wherein the 1-amino-alkylcyclohexane derivative (e.g, neramexane or a pharmaceutically acceptable salt thereof such as neramexane mesylate) is a solid dosage form selected from tablets, tabloids, pills, troches, lozenges, capsules, granules, fine granules, shaped bodies, or pellets.

An additional embodiment of the invention relates to such a titration package wherein three or more dosages are provided in three or more different sets of dosage forms of like dosage, including four or more different dosages in four or more different sets of dosage forms of like dosage.

An additional embodiment of the invention relates to such a titration package wherein each set of dosage forms of like dosage comprises at least five addressable regions (e.g., seven addressable regions or fourteen addressable regions).

An additional embodiment of the invention relates to such a titration package which comprises two or more different doses/dosages of a 1-amino-alkylcyclohexane derivative (e.g., neramexane or a pharmaceutically acceptable salt thereof such as neramexane mesylate), wherein the chemical nature of the derivative is the same for the at least two different dosages, while the amount of the derivative varies between the two different dosages.

An additional embodiment of the invention relates to such a titration package wherein the titration package allows for an up- and/or down-titration of the dosage of the 1-amino-alkylcyclohexane derivative (e.g., neramexane or a pharmaceutically acceptable salt thereof such as neramexane mesylate), until a certain final dosage level is reached.

An additional embodiment of the invention relates to a titration package comprising at least one set of dosage forms of like dosage comprising a 1-amino-alkylcyclohexane derivative (e.g., neramexane or a pharmaceutically acceptable salt thereof such as neramexane mesylate) and at least one second set comprising a placebo.

An additional embodiment of the invention relates to a titration package as defined above wherein the titration package provides for the treatment 1-amino-alkylcyclohexane derivative responsive condition and which provides quick attainment of an effective dose of a composition comprising a 1-amino-alkylcyclohexane derivative (e.g., neramexane or a pharmaceutically acceptable salt thereof such as neramexane mesylate) while minimizing side effects.

DETAILED DESCRIPTION OF THE INVENTION

Figure 1:
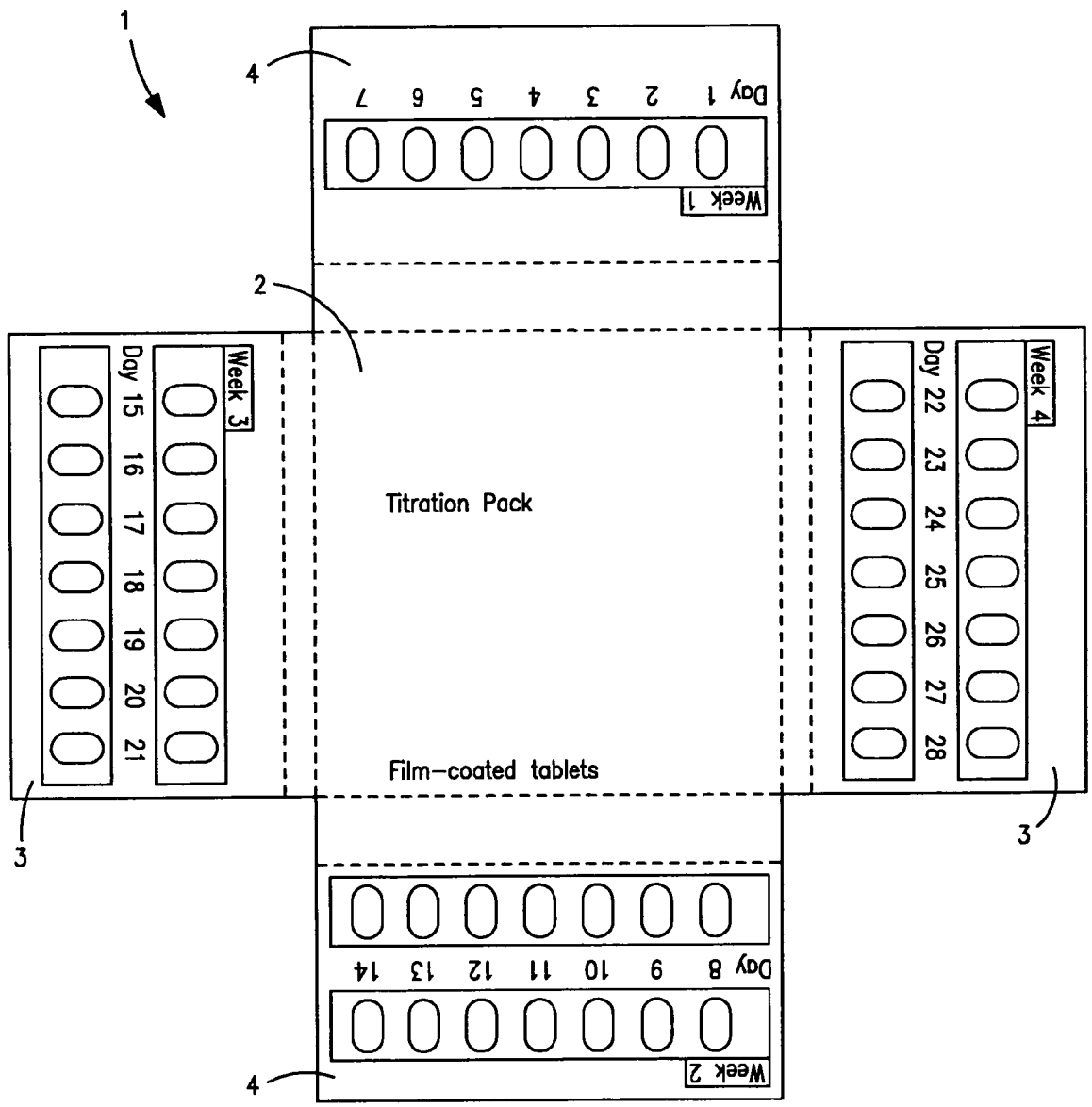
FIGS. 1-4 show the titration package described in Example 3.

As used herein, the term "inner ear disorder" includes, but is not limited to, tinnitus, vertigo, such as paroxymal position vertigo (BPPV), hearing loss inclusive subindications such as acoustic trauma, noise-induced hearing loss, sensorineural hearing loss, mixed hearing loss, unspecified hearing loss, ototoxic hearing loss (ototoxicity), drug-induced hearing loss, environmental chemicals-induced hearing loss, cancer-induced hearing loss, surgical-induced hearing loss, radiation-induced hearing loss, infection-induced hearing loss, sudden (idiopathic) hearing loss, auditory processing disorder, and presbycusis, perilymphatic fistula, secondary endolymphatic hydrops, labyrinthitis and vestibular neuritis, acoustic neuroma, autoimmune inner ear dieses (AIED), chronic ear pain, and Meniere's disease.

Noise-induced hearing loss may be caused by acute or chronic conditions. Long-term exposure to excessive noise is the more common cause of noise-induced hearing loss; however, such hearing loss may also be caused by extremely loud sounds.

Sensorineural hearing loss is due to insensitivity of the inner ear or to impairment of function in the auditory nervous system. Sensorineural hearing loss may be caused by abnormalities in the hair cells of the organ of the Corti in the cochlea.

Ototoxic hearing loss may be caused by medications which damage the ear (i.e., drug-induced hearing loss). Such medications include chemotherapeutic (i.e., anti-neoplastics or anti-cancer) agents (such as cisplatin), aminoglycosides (such as gentamicin), diuretics (such as bumetanide), salicylates (such as aspirin), quinines, NSAIDS, and macrolide antibiotics.

Environmental chemicals-induced hearing loss may be caused by agents (i.e., environmental chemicals) which damage the ear (such as butyl nitrite, mercury or toluene).

Cancer-induced hearing loss may be caused by tumors in the middle ear as well as by other cancers which involve the ear and/or brain.

Surgical-induced hearing loss may occur after otologic or non-otologic surgery; however, the mechanism(s) associated with such hearing loss are not clear.

Radiation-induced hearing loss may be caused by intentional (for example, in radiation therapy) or unintentional exposure to radiation.

Infection-induced hearing loss may be caused by infections involving the inner ear and hearing nerve as well as by infections involving the middle ear. Moreover, there are a number of other types of infections (e.g., mumps, lyme disease, meningitis, herpesvirus infections, fungal infections, bacterial infections, AIDS, and tuberculosis) which may result in hearing loss.

Presbycusis appears to be related, in part, to noise exposure and is characterized by a stiffening of the basilar membrane and deterioration of the hair cells, stria vasularis, ganglion cells, and cochlear nuclei.

As used herein, the term "tinnitus" includes, but is not limited to, all manifestations of subjective and objective tinnitus as well a acute, subacute and chronic forms. It also includes cochlear tinnitus as well as tinnitus associated with hearing loss or mild hearing loss.

The term "subject" as used herein encompasses mammals including animals and humans.

The term 1-amino-alkylcyclohexane derivative is used herein to describe a 1-amino-alkylcyclohexane or a compound derived from 1-amino-alkylcyclohexane, e.g. pharmaceutically acceptable salts of 1-amino-alkylcyclohexanes. The present 1-amino-alkylcyclohexane derivatives may also be described as "1-aminocyclohexane derivatives."

The 1-amino-alkylcyclohexane derivatives of the present invention may be represented by the general formula (I):

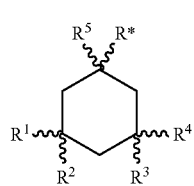

(I)

wherein R* is —$(CH_2)_n$—$(CR^6R^7)_m$—$NR^8R^9$
wherein n+m=0, 1, or 2
wherein $R^1$ through $R^7$ are independently selected from the group consisting of hydrogen and $C_{1-6}$alkyl, wherein $R^8$ and $R^9$ are independently selected from the group consisting of hydrogen and $C_{1-6}$alkyl or together represent lower-alkylene —$(CH_2)_x$— wherein x is 2 to 5, inclusive, and optical isomers, enantiomers, hydrates, and pharmaceutically-acceptable salts thereof.

Non-limiting examples of the 1-amino-alkylcyclohexanes used according to the present invention include:
1-amino-1,3,5-trimethylcyclohexane,
1-amino-1(trans),3(trans),5-trimethylcyclohexane,
1-amino-1(cis),3(cis),5-trimethylcyclohexane,
1-amino-1,3,3,5-tetramethylcyclohexane,
1-amino-1,3,3,5,5-pentamethylcyclohexane (neramexane),
1-amino-1,3,5,5-tetramethyl-3-ethylcyclohexane,
1-amino-1,5,5-trimethyl-3,3-diethylcyclohexane,
1-amino-1,5,5-trimethyl-cis-3-ethylcyclohexane,
1-amino-(1S,5S)cis-3-ethyl-1,5,5-trimethylcyclohexane,
1-amino-1,5,5-trimethyl-trans-3-ethylcyclohexane,
1-amino-(1R,5S)trans-3-ethyl-1,5,5-trimethylcyclohexane,
1-amino-1-ethyl-3,3,5,5-tetramethylcyclohexane,
1-amino-1-propyl-3,3,5,5-tetramethylcyclohexane,
N-methyl-1-amino-1,3,3,5,5-pentamethylcyclohexane,
N-ethyl-1-amino-1,3,3,5,5-pentamethyl-cyclohexane,
N-(1,3,3,5,5-pentamethylcyclohexyl)pyrrolidine,
3,3,5,5-tetramethylcyclohexylmethylamine,
1 amino-1,3,3,5(trans)-tetramethylcyclohexane (axial amino group),
3-propyl-1,3,5,5-tetramethylcyclohexylamine semihydrate,
1-amino-1,3,5,5-tetramethyl-3-ethylcyclohexane,
1-amino-1,3,5-trimethylcyclohexane,
1-amino-1,3-dimethyl-3-propylcyclohexane,
1-amino-1,3(trans),5(trans)-trimethyl-3(cis)-propylcyclohexane,
1-amino-1,3-dimethyl-3-ethylcyclohexane,
1-amino-1,3,3-trimethylcyclohexane,
cis-3-ethyl-1(trans)-3(trans)-5-trimethylcyclohexamine,
1-amino-1,3(trans)-dimethylcyclohexane,
1,3,3-trimethyl-5,5-dipropylcyclohexylamine,
1-amino-1-methyl-3(trans)-propylcyclohexane,
1-methyl-3(cis)-propylcyclohexylamine,
1-amino-1-methyl-3(trans)-ethylcyclohexane,
1-amino-1,3,3-trimethyl-5(cis)-ethylcyclohexane,
1-amino-1,3,3-trimethyl-5(trans)-ethylcyclohexane,
cis-3-propyl-1,5,5-trimethylcyclohexylamine,
trans-3-propyl-1,5,5-trimethylcyclohexylamine,
N-ethyl-1,3,3,5,5-pentamethylcyclohexylamine,
N-methyl-1-amino-1,3,3,5,5-pentamethylcyclohexane,
1-amino-1-methylcyclohexane,
N,N-dimethyl-1-amino-1,3,3,5,5-pentamethylcyclohexane,
2-(3,3,5,5-tetramethylcyclohexyl)ethylamine,
2-methyl-1-(3,3,5,5-tetramethylcyclohexyl)propyl-2-amine,
2-(1,3,3,5,5-pentamethylcyclohexyl)-ethylamine semihydrate,
N-(1,3,3,5,5-pentamethylcyclohexyl)-pyrrolidine,
1-amino-1,3(trans),5(trans)-trimethylcyclohexane,
1-amino-1,3(cis),5(cis)-trimethylcyclohexane,
1-amino-(1R,5S)trans-5-ethyl-1,3,3-trimethylcyclohexane,
1-amino-(1S,5S)cis-5-ethyl-1,3,3-trimethylcyclohexane,
1-amino-1,5,5-trimethyl-3(cis)-isopropyl-cyclohexane,
1-amino-1,5,5-trimethyl-3(trans)-isopropyl-cyclohexane,
1-amino-1-methyl-3(cis)-ethyl-cyclohexane,
1-amino-1-methyl-3(cis)-methyl-cyclohexane,
1-amino-5,5-diethyl-1,3,3-trimethyl-cyclohexane,
1-amino-1,3,3,5,5-pentamethylcyclohexane,
1-amino-1,5,5-trimethyl-3,3-diethylcyclohexane,
1-amino-1-ethyl-3,3,5,5-tetramethylcyclohexane,
N-ethyl-1-amino-1,3,3,5,5-pentamethylcyclohexane,
N-(1,3,5-trimethylcyclohexyl)pyrrolidine or piperidine,
N-[1,3(trans),5(trans)-trimethylcyclohexyl]pyrrolidine or piperidine,
N-[1,3(cis),5(cis)-trimethylcyclohexyl]pyrrolidine or piperidine,
N-(1,3,3,5-tetramethylcyclohexyl)pyrrolidine or piperidine,
N-(1,3,3,5,5-pentamethylcyclohexyl)pyrrolidine or piperidine,
N-(1,3,5,5-tetramethyl-3-ethylcyclohexyl)pyrrolidine or piperidine,
N-(1,5,5-trimethyl-3,3-diethylcyclohexyl)pyrrolidine or piperidine,
N-(1,3,3-trimethyl-cis-5-ethylcyclohexyl)pyrrolidine or piperidine,
N-[(1S,5S)cis-5-ethyl-1,3,3-trimethylcyclohexyl]pyrrolidine or piperidine,
N-(1,3,3-trimethyl-trans-5-ethylcyclohexyl)pyrrolidine or piperidine, N-[(1R,5S)trans-5-ethyl,3,3-trimethylcyclohexyl]pyrrolidine or piperidine,
N-(1-ethyl-3,3,5,5-tetramethylcyclohexyl)pyrrolidine or piperidine,
N-(1-propyl-3,3,5,5-tetramethylcyclohexyl)pyrrolidine or piperidine,
N-(1,3,3,5,5-pentamethylcyclohexyl)pyrrolidine,
and optical isomers, diastereomers, enantiomers, hydrates, their pharmaceutically acceptable salts, and mixtures thereof.

1-Amino-alkylcyclohexane derivatives (e.g., neramexane, 1-amino-1,3,3,5,5-pentamethylcyclohexane) are disclosed in U.S. Pat. Nos. 6,034,134 and 6,071,966. 1-Amino-alkylcyclohexane derivatives (e.g., neramexane) may be used according to the invention in the form of any of pharmaceutically acceptable salts, solvates, isomers, conjugates, and prodrugs, any references to 1-amino-alkylcyclohexane derivatives (e.g., neramexane) in this description should be understood as also referring to such salts, solvates, isomers, conjugates, and prodrugs.

Pharmaceutically acceptable salts include, but are not limited to, acid addition salts, such as those made with hydrochloric, methylsulfonic, hydrobromic, hydroiodic, perchloric, sulfuric, nitric, phosphoric, acetic, propionic, glycolic, lactic, pyruvic, malonic, succinic, fumaric, tartaric, citric, benzoic, carbonic, cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid. All of these salts (or other similar salts) may be prepared by conventional means. The nature of the salt is not critical, provided that it is non-toxic and does not substantially interfere with the desired pharmacological activity.

The term "analog" or "derivative" is used herein in the conventional pharmaceutical sense, to refer to a molecule that structurally resembles a reference molecule (such as neramexane), but has been modified in a targeted and controlled manner to replace one or more specific substituents of the referent molecule with an alternate substituent, thereby generating a molecule which is structurally similar to the reference molecule. Synthesis and screening of analogs (e.g., using structural and/or biochemical analysis), to identify slightly modified versions of a known compound which may have improved or biased traits (such as higher potency and/or selectivity at a specific targeted receptor type, greater ability to penetrate mammalian blood-brain barriers, fewer side effects, etc.) is a drug design approach that is well known in pharmaceutical chemistry.

The term "treat" is used herein to mean to relieve or alleviate at least one symptom of a disease or a condition in a subject. Within the meaning of the present invention, the term "treat" also denotes to arrest, delay the onset (i.e., the period prior to clinical manifestation of a disease) and/or reduce the risk of developing or worsening a disease.

The term "therapeutically effective" applied to dose or amount refers to that quantity of a compound or pharmaceutical composition that is sufficient to result in a desired activity upon administration to a mammal in need thereof.

The phrase "pharmaceutically acceptable", as used in connection with the 1-amino-alkylcyclohexane derivative of the invention, refers to molecular entities and other ingredients of e.g. pharmaceutical compositions that are physiologically tolerable and do not typically produce untoward reactions when administered to a mammal (e.g., human). Typically, as used herein, the term "pharmaceutically acceptable" means approved by a regulatory agency or listed in a generally recognized pharmacopeia for use in mammals, and more particularly in humans.

The term "carrier" applied to pharmaceutical compositions of the invention refers to a diluent, excipient, or vehicle with which an active compound (e.g., neramexane) is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Such carriers can also be solids, for example excipients as described below. Suitable pharmaceutical carriers are described in "Remington's Pharmaceutical Sciences" by A. R. Gennaro, 20$^{th}$ Edition.

The term "about" or "approximately" usually means within 20%, alternatively within 10%, including within 5% of a given value or range.

The term "titration scheme" is meant to be a method of treatment as discussed herein, wherein patients are treated for a disease or a condition wherein at least two different dosages (doses) of one or more 1-amino-alkylcyclohexane derivatives, e.g. in the form of a pharmaceutical compositions useful in treating such condition are administered in a step-wise manner in a once daily or multiple times per day manner and wherein lower doses are administered earlier in the treatment and higher doses are administered during subsequent treatment weeks. Optionally, in those treatment weeks wherein different dosages are administered on the same day, the titration scheme may provide for the administration of a lower dosage in the morning and a higher dosage in the evening, thereby minimizing drug-induced side effects during the most productive hours of the day.

The 1-amino-alkylcyclohexane derivative (e.g., neramexane, such as neramexane mesylate) or a pharmaceutical composition comprising the same may be used for the treatment of an inner ear disorder according to the titration scheme according to the invention. In one embodiment the derivative and/or pharmaceutical composition (medicament) are adapted to or appropriately prepared for a specific administration scheme as disclosed herein. For this purpose the package and/or the package leaflet and/or the patient information and/or the dosage form itself may contain corresponding information.

The active ingredient (e.g., neramexane such as neramexane mesylate) or the composition of the present invention may be used for the manufacture of a medicament for the treatment of tinnitus, wherein the medicament is adapted to or appropriately prepared for a specific administration as disclosed herein. For this purpose the package leaflet and/or the patient information contains corresponding information.

The term "titration package" is meant to be any substrate, container or packaging that provides at least two dosages (doses) of a at least 1-amino-alkylcyclohexane. The dosages (doses) may be the same or different. When being used for e.g. treating an inner ear disorder according to the titration scheme of the present invention the package comprises information regarding the dosing of the 1-amino-alkylcyclohexane. Said information may be provided in or on the package, via the package leaflet/user information within the package and/or via the dosages themselves, e.g. by using a different appearance, such as a different shape and/or color for different dosages of the 1-amino-alkylcyclohexane derivative.

Providing two (chemically) different pharmaceutical compositions (in particular in regard to the single active ingredients thereof) in formally the same amount within one titration package is also within the scope of "providing two different dosages".

In one embodiment the titration package may be any package that is able to contain and/or affix the 1-amino-alkylcyclohexane derivative, e.g. in the form of a pharmaceutical composition as provided in any conceivable form at individually addressable regions that are part of the package. The "addressable regions" should be identifiable by the user of the package.

In the context of the present invention, a "set" means any arrangement of three or more addressable regions of any type as arranged on a two or three-dimensional substrate.

In the context of the present invention, an "addressable region" is understood to mean any region on a two- or three-dimensional substrate that is part of a set and can be reproducibly differentiated from any other addressable region by a user of the titration package. Two adjacent addressable regions within a set and/or between two sets may be physically separated from each other, i.e. do not overlap and/or do not touch each other.

In accordance with the present invention, no limitations exist as to how two different addressable regions are made addressable/identifiable. The addressable regions may be differentiated from each other by at least one means selected from the following group, or any combination thereof: highlighting by color and/or shading and/or imprint, provision of a blister pack at the position of the addressable region the blister pack then being the addressable region; provision of an indentation/elevation; provision of a different material or a gradient in material, provision of a pouch or other conceivable (sub-)containment for a 1-amino-alkylcyclohexane.

In accordance with the present invention, the addressable regions may also be defined by the 1-amino-alkylcyclohexane derivative (e.g., neramexane or a pharmaceutically acceptable salt thereof), which may be in the form of a pharmaceutical composition, which is present in the form of solids, including pills, capsules, tablets, lozenges or troches, that are directly or indirectly attached to or adhered to the package or parts thereof. It is also within the scope of the present invention that individual addressable regions of a set may comprise a "blank" (i.e., at least one addressable region does not contain a pharmaceutical composition).

In accordance with the present invention, the term "row" is understood to mean any arrangement of three or more (e.g., five or more, 7 or more, 10 or more) addressable regions on a substrate, wherein the regions are essentially arranged along a horizontal line (assuming that the row is seen in top view and the standard coordinate system is applied). It is within the scope of the present invention if addressable regions of the row are shifted, staggered, offset or slightly displaced relative to each other, as long as the overall assembly of addressable regions essentially follows such a horizontal pattern.

In accordance with the present invention, the term "column" is understood to mean any arrangement of three or more (e.g., five or more, 7 or more, 10 or more) addressable regions on a substrate, wherein the regions are essentially arranged along a vertical line (assuming that the row is seen in top view and the standard coordinate system is applied). It is within the scope of the present invention if addressable regions of the column are shifted, staggered, offset or slightly displaced relative to each other, as long as the overall assembly of addressable regions essentially follows such a vertical pattern.

According to the present invention, the dosage form of the 1-amino-alkylcyclohexane derivative (e.g., neramexane or a pharmaceutically acceptable salt thereof) may be a solid formulation including a capsule, a tablet, or the like (see Remington's Pharmaceutical Sciences, 20$^{th}$ Edition, by A. R. Gennaro).

The 1-amino-alkylcyclohexane derivatives of the present invention may be administered orally as a semi-solid, or liquid formulation (see Remington's Pharmaceutical Sciences, 20$^{th}$ Edition, by A. R. Gennaro).

For solid formulations in the form of a tablet or capsule, the 1-amino-alkylcyclohexane derivatives of the present invention (e.g., neramexane or a pharmaceutically acceptable salt thereof) may be combined with non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, and the like.

The tablets may be coated with a concentrated sugar solution which may contain e.g., gum arabic, gelatine, talcum, titanium dioxide, and the like. Alternatively, the tablets can be coated with a polymer that dissolves in a readily volatile organic solvent or mixture of organic solvents. In specific embodiments, neramexane is formulated in immediate-release (IR) or modified-release (MR) tablets. Immediate release solid dosage forms permit the release of most or all of the active ingredient (e.g. 90% or more) over a short period of time, such as 60 minutes or less, and make rapid absorption of the drug possible (immediate release formulations of 1-amino-alkylcyclohexanes such as neramexane are disclosed in US Published Application Nos. 2006/0002999 and 2006/0198884, the subject matter of which relating to immediate release formulations is hereby incorporated by reference). Modified release solid oral dosage forms permit the sustained release of the active ingredient over an extended period of time in an effort to maintain therapeutically effective plasma levels over similarly extended time intervals and/or to modify other pharmacokinetic properties of the active ingredient (modified release formulations of neramexane are disclosed in US Published Application No. 2007/0141148, the subject matter of which is hereby incorporated by reference). For example, neramexane mesylate may be formulated in a modified release dosage form (including modified release tablets) to provide a 50 mg dose of neramexane mesylate.

For the formulation of soft gelatin capsules, the 1-amino-alkylcyclohexane derivatives of the present invention (e.g., neramexane) may be admixed with e.g., a vegetable oil or poly-ethylene glycol. Hard gelatin capsules may contain granules of the active substances using either the above mentioned excipients for tablets e.g., lactose, saccharose, sorbitol, mannitol, starches (e.g., potato starch, corn starch or amylopectin), cellulose derivatives or gelatine. Also liquids or semisolids of the drug can be filled into hard gelatine capsules.

The 1-amino-alkylcyclohexane derivatives of the present invention (e.g., neramexane) can also be introduced in microspheres or microcapsules, e.g., fabricated from polyglycolic acid/lactic acid (PGLA) (see, e.g., U.S. Pat. Nos. 5,814,344; 5,100,669 and 4,849,222; PCT Publications No. WO 95/11010 and WO 93/07861). Biocompatible polymers may be used in achieving controlled release of a drug, include for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

Formulation of the 1-amino-alkylcyclohexane derivatives of the present invention in a semi-solid or liquid form may also be used. The 1-amino-alkylcyclohexane derivative (e.g., neramexane) may constitute between 0.1 and 99% by weight of the formulation, more specifically between 0.2 and 50% by weight for formulations suitable for oral administration.

In one embodiment of the invention, the 1-amino-alkylcyclohexane derivative (e.g., neramexane) is administered in a modified release formulation. Modified release dosage forms provide a means for improving patient compliance and for ensuring effective and safe therapy by reducing the incidence of adverse drug reactions. Compared to immediate release dosage forms, modified release dosage forms can be used to prolong pharmacologic action after administration, and to reduce variability in the plasma concentration of a drug throughout the dosage interval, thereby eliminating or reducing sharp peaks.

A modified release form dosage may comprise a core either coated with or containing a drug. The core being is then coated with a release modifying polymer within which the drug is dispersed. The release modifying polymer disintegrates gradually, releasing the drug over time. Thus, the outermost layer of the composition effectively slows down and thereby regulates the diffusion of the drug across the coating layer when the composition is exposed to an aqueous environment, i.e. the gastrointestinal tract. The net rate of diffusion of the drug is mainly dependent on the ability of the gastric fluid to penetrate the coating layer or matrix and on the solubility of the drug itself.

In another embodiment of the invention, the 1-amino-alkylcyclohexane derivative (e.g., neramexane) is formulated in an oral, liquid formulation. Liquid preparations for oral administration can take the form of, for example, solutions, syrups, emulsions or suspensions, or they can be presented as a dry product for reconstitution with water or other suitable vehicle before use. Preparations for oral administration can be suitably formulated to give controlled or postponed release of the active compound. Oral liquid formulations of 1-amino-alkylcyclohexanes, such as neramexane, are described in PCT International Application No. PCT/US2004/037026, the subject matter of which is hereby incorporated by reference.

For oral administration in liquid form, 1-amino-alkylcyclohexane derivatives of the present invention (e.g., neramexane) may be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (BHA, BHT, propyl gallate, sodium ascorbate, citric acid) can also be added to stabilize the dosage forms. For example, solutions may contain from about 0.2% to about 20% by weight of neramexane, with the balance being sugar and mixture of ethanol, water, glycerol and propylene glycol. Optionally, such liquid formulations may contain coloring agents, flavoring agents, saccharine and carboxymethyl-cellulose as a thickening agent or other excipients.

In another embodiment, a therapeutically effective amount of a 1-amino-alkylcyclohexane derivative (e.g., neramexane) is administered in an oral solution containing a preservative, a sweetener, a solubilizer, and a solvent. The oral solution may include one or more buffers, flavorings, or additional excipients. In a further embodiment, a peppermint or other flavoring is added to the neramexane derivative oral liquid formulation.

The invention also provides a pharmaceutical pack or kit comprising one or more containers containing a 1-amino-alkylcyclohexane derivative (e.g., neramexane) and, optionally, more of the ingredients of the formulation. In a specific embodiment, neramexane is provided as an oral solution (2 mg/ml) for administration with the use of a 2 teaspoon capacity syringe (dosage KORC®). Each oral syringe has blue hatch marks for measurement, with lines on the right side of the syringe (tip down) representing tsp units, and those on the left representing ml units.

The optimal therapeutically effective amount may be determined experimentally, taking into consideration the exact mode of administration in which the drug is administered, the indication toward which the administration is directed, the subject involved (e.g., body weight, health, age, sex, etc.), and the preference and experience of the physician or veterinarian in charge.

Toxicity and therapeutic efficacy of the 1-amino-alkylcyclohexane derivatives of the invention may be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it may be expressed as the ratio $LD_{50}/ED_{50}$. 1-Amino-alkylcyclohexane derivatives/compositions that exhibit large therapeutic indices are preferred.

Suitable daily doses of the active compounds of the invention in therapeutic treatment of humans are about 0.01-10 mg/kg bodyweight on peroral administration and 0.001-10 mg/kg bodyweight on parenteral administration. For example, for adults, suitable daily doses of neramexane mesylate include doses of 50 mg and 75 mg per day. An equimolar amount of another pharmaceutically acceptable salt, a solvate, an isomer, a conjugate, a prodrug or a derivative thereof, such as neramexane hydrochloride, is also suitable.

The daily doses indicated herein may be administered, for example, as one or two dosing units once, twice or three times per day. Suitable doses per dosage unit may therefore be the daily dose divided (for example, equally) between the number of dosage units administered per day, and will thus typically be about equal to the daily dose or one half, one third, one quarter or one sixth thereof. Dosages per dosage unit may thus be calculated from each daily dosage indicated herein. A daily dose of 5 mg, for example may be seen as providing a dose per dosage unit of, for example, about 5 mg, 2.5 mg, 1.67 mg, 1.25 mg and 0.83 mg, depending upon the dosing regimen chosen. Correspondingly, a dosage of 150 mg per day corresponds to dosages per dosing unit of, for example, about 150 mg, 75 mg, 50 mg, 37.5 mg, and 25 mg for corresponding dosing regimens.

Treatment duration may be short-term, e.g., several weeks (for example 8-14 weeks), or long-term until the attending physician deems further administration no longer is necessary.

EXAMPLES OF REPRESENTATIVE FORMULATIONS

With the aid of commonly used solvents, auxiliary agents and carriers, active ingredients may be processed into solutions, tablets, coated tablets, capsules, and the like. Tablets suitable for oral administration may be prepared by conventional tabletting techniques. The following examples are given by way of illustration only and are not to be construed as limiting.

Formulation Example 1

Neramexane Mesylate Immediate Release Tablets

Tables 1-4 provide the make-up of neramexane immediate release tablets in 12.5, 25.0, 37.5, and 50.0 mg dosages, including active components, coating agents, and other excipients.

TABLE 1

Neramexane mesylate, 12.5 mg film coated tablets

| Component | Amount [mg] | Function |
|---|---|---|
| Neramexane mesylate | 12.50 | Active pharmaceutical ingredient |
| Cellulose microcrystalline | 103.25 | Binder |
| Croscarmellose sodium | 6.25 | Disintegrant |
| Silicon dioxide, colloidal | 1.25 | Flow promoter |
| Talc | 1.25 | Glident |
| Magnesium stearate | 0.50 | Lubricant |
| core weight | 125.00 | |
| Coating (HPMC), Opadry or Sepifilm | 5.00 | Coating |
| Coat weight | 5.00 | |
| coated tablet total weight | 130.00 | |

TABLE 2

Neramexane mesylate, 25.0 mg film coated tablets

| Component | Amount [mg] | Function |
|---|---|---|
| Neramexane mesylate | 25.00 | Active pharmaceutical ingredient |
| Cellulose microcrystalline | 206.50 | Binder |
| Croscarmellose sodium | 12.5 | Disintegrant |
| Silicon dioxide, colloidal | 2.50 | Flow promoter |
| Talc | 2.50 | Glident |
| Magnesium stearate | 1.00 | Lubricant |
| core weight | 250.00 | |
| Coating (HPMC), Opadry or Sepifilm | 10.00 | Coating |
| Coat weight | 10.00 | |
| coated tablet total weight | 260.00 | |

TABLE 3

Neramexane mesylate, 37.5 mg film coated tablets

| Component | Amount [mg] | Function |
|---|---|---|
| Neramexane mesylate | 37.50 | Active pharmaceutical ingredient |
| Cellulose microcrystalline | 309.75 | Binder |
| Croscarmellose sodium | 18.75 | Disintegrant |
| Silicon dioxide, colloidal | 3.75 | Flow promoter |
| Talc | 3.75 | Glident |
| Magnesium stearate | 1.50 | Lubricant |
| core weight | 375.00 | |
| Coating (HPMC), Opadry or Sepifilm | 15.00 | Coating |
| Coat weight | 15.00 | |
| coated tablet total weight | 390.00 | |

TABLE 4

Neramexane mesylate, 50.0 mg film coated tablets

| Component | Amount [mg] | Function |
|---|---|---|
| Neramexane mesylate | 50.00 | Active pharmaceutical ingredient |
| Cellulose microcrystalline | 413.00 | Binder |
| Croscarmellose sodium | 25.00 | Disintegrant |
| Silicon dioxide, colloidal | 5.00 | Flow promoter |
| Talc | 5.00 | Glident |
| Magnesium stearate | 2.00 | Lubricant |
| core weight | 500.00 | |
| Coating (HPMC), Opadry or Sepifilm | 20.00 | Coating |
| Coat weight | 20.00 | |
| coated tablet total weight | 520.00 | |

Formulation Example 2

Neramexane Mesylate Oral Solution

Table 5 provides the make-up of a neramexane oral solution in 2, 5, 10, and 20 mg/mL strengths.

TABLE 5

Neramexane Oral Solution

| Ingredients | 2 mg/mL % w/v | 5 mg/ml % w/v | 10 mg/ml % w/v | 20 mg/mL % w/v |
|---|---|---|---|---|
| Neramexane Mesylate | 0.2 | 0.5 | 1.0 | 2.0 |
| Sorbitol Solution, USP, 70% | 30.0 | 30.0 | 30.0 | 30.0 |
| Methylparaben, NF | 0.10 | 0.10 | 0.10 | 0.10 |
| Propylparaben, NF | 0.01 | 0.01 | 0.01 | 0.01 |
| Propylene Glycol, USP | 2.5 | 2.5 | 2.5 | 2.5 |
| Glycerin, USP | 10.0 | 10.0 | 10.0 | 10.0 |
| Flavor, Natural Peppermint #104 | 0.5 | 0.5 | 0.5 | 0.5 |
| Citric Acid, USP, Anhydrous | 0.19 | 0.19 | 0.19 | 0.19 |
| Sodium Citrate, USP, Dihydrate | 0.88 | 0.88 | 0.88 | 0.88 |
| Purified Water, USP | QS | QS | QS | QS |

EXAMPLES

The following examples illustrate the invention without limiting its scope.

Example 1

Double Blind Placebo Controlled Pilot Trial of Neramexane for Treatment of Tinnitus The objective of this pilot project was to conduct a clinical trial to assess the efficacy of neramexane as a treatment for tinnitus. The primary objective of this study was to compare the efficacy, tolerability and safety of neramexane mesylate at three different dosages (25, 50 or 75 mg/d) with placebo in subjects with subjective tinnitus of at least moderate severity.

Study Design

In a double-blind, multicenter, randomized, placebo-controlled, parallel-group study, the efficacy of neramexane in subjects suffering from tinnitus of at least moderate severity was assessed. Approximately 100 patients, who fulfilled particular inclusion criteria and met none of particular exclusion criteria, were randomized to each of four double-blind treatment groups (neramexane mesylate 25, 50, 75 mg/d or placebo), resulting in approximately 400 patients in total.

The double-blind, 16-week treatment period consisted of a 4-week uptitration period and a 12-week fixed-dose treatment period at unchanged maintenance b.i.d. dosing. In case of poor tolerability, however, the investigator could consider a dose reduction by 25 mg/d (or placebo, respectively). After the treatment phase, there was a 4-week follow-up period with no active treatment and concomitant therapy restrictions. In total, this study involved seven study visits: screening, baseline, and at the end of weeks 4, 8, 12, 16, and 20. (Participants received either neramexane mesylate (e.g. 50 mg, as 25 mg immediate release tablets given twice daily) or placebo twice daily for 16 weeks. Neramexane mesylate was uptitrated in weekly steps of 12.5 or 25 mg during a 4-week uptitration period preceding the fixed-dose 12-week treatment period. Treatment was followed by a four week follow-up period.)

The scheduled visits for evaluation of each patient were as follows:

Visit 1 (screening): After signing the consent form, the subject underwent a physical examination and clinical laboratory testing. Patient eligibility for the study was evaluated via a check of inclusion/exclusion criteria. An initial Tinnitus Interview was conducted. The subject also completed a Tinnitus-Beeinträchtigungs-Fragebogen (THF-12) (i.e., a 12-item German modified and validated version (Greimel K V et al., Tinnitus-Beeinträchtigungs-Fragebogen (THF-12). Manual. Frankfurt am Main: Swets & Zeitlinger B. V.; 2000) of the 25-item Tinnitus Handicap Inventory or THI (Newman C W, et al. Development of the Tinnitus Handicap Inventory. Arch Otolaryngol Head Neck Surg 1996; 122(2): 143-148; Newman C W, et al. Psychometric adequacy of the Tinnitus Handicap Inventory (THI) for evaluating treatment outcome. J Am Acad Audiol 1998; 9(2): 153-160.)), a Hospital Anxiety and Depression Scale-Depression Subscale (HADS-D) Questionnaire and a Hyperacusis (Geräuschüberempfindlichkeit-Fragenbogen (GÜF)) Questionnaire (if applicable).

Visit 2 (baseline): The subject was asked about adverse events and changes in concomitant medication/disease, which events/changes were documented. The subject was evaluated for study eligibility based on a review of the inclusion/exclusion criteria. Trial procedures as well as allowed and forbidden concomitant medications were reviewed with the subject. An initial Tinnitus Interview was conducted. The subject also completed a THF-12, HADS-D Questionnaire and GÜF Questionnaire (if applicable). The subject was enrolled in the study and study medication (placebo or neramexane) was dispensed as described below.

Visit 3 (Week 4): This visit occurred at the end of the 4-week up-titration sequence. The subject was asked about adverse events and changes in concomitant medication/disease, which events/changes were documented. A follow-up Tinnitus Interview was conducted. The subject also completed a THF-12, HADS-D Questionnaire and GÜF Questionnaire (if applicable). Medication compliance was assessed, and medication for the next 4 weeks was dispensed as described below.

Visit 4 (Week 8): This visit occurred at the end of the first 4-week fixed-dose double-blind treatment period. The subject was asked about adverse events and changes in concomitant medication/disease, which changes are documented. Blood samples were collected in order to determine neramexane pre-dose concentration. A follow-up Tinnitus Interview was conducted. The subject also completed a THF-12, HADS-D Questionnaire and GÜF Questionnaire (if applicable). Medication compliance was assessed and, medication for the next 4 weeks was dispensed as described below.

Visit 5 (Week 12): This visit occurred at the end of the second 4-week fixed-dose double-blind treatment period. The subject was asked about adverse events and changes in concomitant medication/disease, which changes are documented. A follow-up Tinnitus Interview was conducted. The subject also completed a THF-12, HADS-D Questionnaire and GÜF Questionnaire (if applicable). Medication compliance was assessed and, medication for the next 4 weeks was dispensed as described below.

Visit 6 (Week 16, end of treatment). This visit occurred at the end of the 12-week fixed-dose double-blind treatment period. The subject was asked about adverse events and changes in concomitant medication/disease, which changes are documented. A clinical laboratory evaluation was performed. A follow-up Tinnitus Interview was conducted, and the subject completed a THF-12, HADS-D Questionnaire and GÜF Questionnaire (if applicable). Pure-tone audiometry (air conduction) was also conducted.

Visit 7 (Week 20): This visit occurred at the end of the 4-week follow-up period after the last study medication dose. Review of concomitant medications as well as the occurrence of adverse events since the last visit is conducted with subject. A follow-up Tinnitus Interview was conducted, and the subject completed a THF-12, HADS-D Questionnaire and GÜF Questionnaire (if applicable).

Administration of Neramexane

Neramexane mesylate immediate release tablets (12.5 mg and 25 mg) and matching placebo tablets were administered as film coated tablets.

Medication was supplied in blister boxes that were dispensed from Visit 2 to Visit 5. Each blister box contained 4 blister cards for 4 treatment weeks and 1 blister card as reserve. Blister cards were identified by treatment weeks. Daily medication within the blister cards were identified per day. Study medication for each study day consisted of 4 separate tablets. One blister card consisted of 32 tablets (7 days, 4 tablets per day and one day reserve, 4 tablets per day). One package of medication per patient consisted of 5 boxes. Box 2 was added as reserve medication for box 1 (uptitration period) and was only to be dispensed if the subject lost a blister card of box 1 or the whole box.

Study medication was dispensed at Visit 2 (baseline, day 0). Each patient received one blister box containing 5 blister cards (including one reserve blister) of double-blind study medication (i.e., 32 tablets). Subjects were instructed to take 2 tablets twice daily (4 tablets/d), beginning the day after dispensing of the study medication, until they returned for their next study visit (Visit 3). For those subjects assigned to receive active medication, some placebo tablets were incorporated into the dosing regimen to ensure blinding during the uptitration period. The target fixed-maintenance dose of 25, 50, or 75 mg/d was administered starting with the fifth week of double-blind treatment and was continued throughout the study. At each of the subsequent visits (Visits 3, 4, and 5, corresponding to end of week 4, 8 and 12) patients received another blister box containing 5 blister cards for the 4 week intervals, with double-blind medication for the intervening treatment period until the next study visit. The dosing schedule is shown in Table 6.

Throughout the double-blind treatment period, patients were to continue to take 2×2 tablets of medication daily at a constant interval of 12 hours. In case the patient had already taken the morning dose of study medication on the day of Visits 4 and 6 (Week 8 and Week 16), no scheduled blood sampling was to be done. The investigator had to re-dispense a sufficient amount of study medication. The patient should continue to take 2 by 2 tablets at a constant interval of 12 hours and had return for pre-dose Neramexane blood sampling within the time window of Visits 4 and 6.

TABLE 6

Administration of Neramexane mesylate

| Treatment group | 4-week double-blind up-titration period | | | | 12-week fixed-dose double-blind period | 4-week follow-up |
| --- | --- | --- | --- | --- | --- | --- |
| | Week 1 | Week 2 | Week 3 | Week 4 | Weeks 5-16 | Weeks 17-20 |
| High-dose | 12.5/0 | 12.5/12.5 | 25/12.5 | 25/25 | 37.5/37.5 (75 mg/d) | — |
| Medium-dose | 12.5/0 | 12.5/0 | 12.5/12.5 | 25/12.5 | 25/25 (50 mg/d) | — |
| Low-dose | 12.5/0 | 12.5/0 | 12.5/0 | 12.5/0 | 12.5/12.5 (25 mg/d) | — |
| Placebo | 0/0 | 0/0 | 0/0 | 0/0 | 0/0 | — |

(xx/xx) refers to the morning/evening dose in mg, respectively

In case of poor tolerability the investigator could consider a dose reduction of 25 mg/d by omitting the bigger tablet in the morning which constituted an effective dose reduction only in the 75 mg/d and 50 mg/d neramexane mesylate groups. After omitting the bigger tablet (25 mg or placebo, respectively) of the morning dose, these patients could then continue the course of the study as scheduled, while receiving only one smaller tablet as the morning dose (12.5 mg or placebo, respectively) and 2 tablets of different sizes (12.5 mg, 25 mg or placebo, respectively) as the evening dose. The dose was to be kept stable until the end of the study.

Subjects were instructed to take study medication always at an individually convenient, but stable time point throughout the study course and at a constant dosing interval of 12 hours whenever possible (e.g. 6:00 h and 18:00 h or 8:00 h and 20:00 h). At each study visit, the investigator enquired the time points of study medication intake on the preceding day. At the end of week 4, 8, 12, and 16 (or upon early termination), patients returned to the study site bringing their blister boxes containing 5 blister cards with them for an assessment of medication compliance.

Efficacy
Primary Outcome
The change in THF-12 total score from baseline (Visit 2) to the endpoint visit (Visit 6, i.e. Week 16) was the primary efficacy endpoint in this study.

Secondary Outcomes
THF-12 total score (values and absolute change from baseline) at all post-baseline visits except the endpoint visit.
Change in the THF-12 total score from Week 16 to Week 20 (values and absolute changes).
THF-12 factorial scores (values and absolute change from baseline, including the change from Week 16 to Week 20) at all post-baseline visits.
Hyperacusis questionnaire GÜF ("Geräuschüberempfindlichkeits-Fragebogen"), values and absolute change from baseline, including the change from Week 16 to Week 20, total and factorial scores at all post-baseline visits if hyperacusis was present.
Clinical global impression of change: item 27 of the tinnitus follow-up interview was summarized after dichotomization of the responses in any improvement (values 1, 2, 3) versus no improvement (values 4, 5, 6, 7) and in marked improvement (values 1, 2) versus no marked improvement (values 3, 4, 5, 6, 7).
Total score of HADS-D as well as the depression and anxiety subscale scores (values and absolute change from baseline, also the change from week 16 to week 20) at all post-baseline visits.
Values of tinnitus interview (initial and follow-up) at all post-baseline visits; absolute change from baseline and change from Week 16 to Week 20 for items 8, 9, 10, 19, 20, 21, 24, 25 and 26 of the follow-up interview.

Data Analysis
All efficacy analyses were performed on the ITT population using the last-observation-carried-forward (LOCF) approach. For sensitivity purposes an analysis of the per-protocol set and of observed cases was performed additionally. All statistical tests used for testing the primary efficacy (confirmatory testing) and secondary efficacy criteria (exploratory), and all other statistical tests used for exploratory analyses were two-sided hypothesis tests performed at the 5% significance level. For all variables standard descriptive statistics were calculated.

Change from baseline (Visit 2) to Week 16 in THF-12 total score was analyzed using a two-way ANCOVA model with treatment group and study centers as factors and baseline THF-12 total score as covariate.

For secondary efficacy parameters, the comparison between neramexane and placebo was performed, if appropriate, by visit using a two-way ANCOVA with treatment group and study center as factors and the corresponding baseline value of the efficacy parameter as covariate.

Discussion
This clinical study showed promising results in terms of efficacy and safety. Moreover, this study also demonstrated that the dosing schedule shown in Table 6 provided for an acceptable rate of AE-related dropouts even at the 75 mg/d dose. These results are shown in Table 7.

TABLE 7

Frequency of patients with most common treatment emergent adverse events leading to drop-out by preferred term (EFS)

| Preferred term[1] (MedDRA 9.1) | Placebo (N = 112) | | 25 mg/d Neramexane (N = 108) | | 50 mg/d Neramexane (N = 107) | | 75 mg/d Neramexane (N = 102) | |
| --- | --- | --- | --- | --- | --- | --- | --- | --- |
| | n | % | n | % | n | % | n | % |
| Any adverse event leading to drop-out | 15 | (13.4) | 9 | (8.3) | 23 | (21.5) | 29 | (28.4) |
| Dizziness | 4 | (3.6) | 2 | (1.9) | 6 | (5.6) | 15 | (14.7) |
| Vertigo | 1 | (0.9) | 0 | (0.0) | 4 | (3.7) | 3 | (2.9) |
| Fatigue | 0 | (0.0) | 0 | (0.0) | 2 | (1.9) | 2 | (2.0) |
| Headache | 3 | (2.7) | 0 | (0.0) | 1 | (0.9) | 2 | (2.0) |
| Hyperhidrosis | 1 | (0.9) | 0 | (0.0) | 0 | (0.0) | 2 | (2.0) |
| Influenza | 0 | (0.0) | 0 | (0.0) | 0 | (0.0) | 2 | (2.0) |
| Nausea | 1 | (0.9) | 0 | (0.0) | 2 | (1.9) | 2 | (2.0) |
| Visual acuity reduced | 0 | (0.0) | 0 | (0.0) | 0 | (0.0) | 2 | (2.0) |
| Tinnitus | 0 | (0.0) | 2 | (1.9) | 0 | (0.0) | 1 | (1.0) |
| Paresthesia | 0 | (0.0) | 0 | (0.0) | 2 | (1.9) | 0 | (0.0) |
| Depression | 1 | (0.9) | 1 | (0.9) | 2 | (1.9) | 0 | (0.0) |
| Cardiovascular disorder | 0 | (0.0) | 0 | (0.0) | 2 | (1.9) | 0 | (0.0) |

[1]Occurring in at least 2 patients of any treatment group
EFS = evaluable for safety,
N = number of patients in respective treatment group,
n = number of patients with treatment emergent adverse event leading to drop-out
Calculation of percentages based on N.

These findings demonstrate that the dosing schedule shown in Table 6 or in the proposed dosing schedule shown in Table 8 below allow for an individual titration to a body weight-adjusted target dose of 50 mg/day up to 90 kg body weight or 75 mg/day for patients with a body weight of ≥90 kg.

TABLE 8

Proposed Dosing Schedule for Neramexane Mesylate

| Treatment group | Double-blind period Week | | | | |
| --- | --- | --- | --- | --- | --- |
| | 1 | 2 | 3 | 4 | 5-17 (13 weeks) |
| Neramexane 50 mg | 0 (Pbo)/12.5 | 12.5/12.5 | 12.5/25 | 25/25 | 25/25 |
| Neramexane 75 mg* | 0 (Pbo)/12.5 | 12.5/12.5 | 12.5/25 | 25/25 | 37.5/37.5 |
| Placebo | 0/0 | 0/0 | 0/0 | 0/0 | 0/0 |

After intake of a four week uptitration package, patients may continue with a maintenance dose of either 50 or 75 mg neramexane mesylate per day. For example, patients starting a treatment with neramexane begin with a 4-week starter kit (i.e., titration package) and then switch to b.i.d. application of 25 or 37.5 mg tablets depending on their body weight in order to get a daily maintenance dose of 50 or 75 mg. Thus, the proposed dosing schedule shown in Table 8 allows for two different, e.g. weight adapted maintenance doses, at week 5.

Example 2

Double Blind Placebo Controlled Trial of Neramexane for Treatment of Tinnitus The objective of this project is to conduct a clinical trial to further assess the efficacy of neramexane as a treatment for tinnitus. The primary objective of this study is to compare the efficacy, tolerability and safety of neramexane mesylate with placebo in subjects with first onset, persistent, unilateral or bilateral subjective tinnitus.

Study Design

In a double-blind, multicenter, randomized, placebo-controlled, parallel-group study, the efficacy of neramexane in subjects suffering from tinnitus is assessed. Patients, who fulfill particular inclusion criteria and meet none of particular exclusion criteria, are randomized into double-blind treatment groups.

The double-blind, 16-week treatment period consists of a 4-week uptitration period and a 12-week fixed-dose treatment period at unchanged maintenance dosing. In case of poor tolerability, however, the investigator may consider a dose reduction by 25 mg/d. After the treatment phase, there is a 4-week follow-up period with no active treatment and concomitant therapy restrictions. In total, this study involves seven study visits: screening, baseline, and at the end of weeks 4, 8, 12, 16, and 20.

The scheduled visits for evaluation of each patient are as follows:

Visit 1 (screening): After signing the consent form, the subject undergoes a physical examination and clinical laboratory testing. Patient eligibility for the study is evaluated via a check of inclusion/exclusion criteria. An initial Tinnitus Interview is conducted. The subject also completes a Tinnitus-Beeinträchtigungs-Fragebogen (THF-12) (i.e., a 12-item German modified and validated version (Greimel K V et al., Tinnitus-Beeinträchtigungs-Fragebogen (THF-12). Manual. Frankfurt am Main: Swets & Zeitlinger B. V.; 2000) of the 25-item Tinnitus Handicap Inventory or THI (Newman C W, et al. Development of the Tinnitus Handicap Inventory. Arch Otolaryngol Head Neck Surg 1996; 122(2): 143-148; Newman C W, et al. Psychometric adequacy of the Tinnitus Handicap Inventory (THI) for evaluating treatment outcome. J Am Acad Audiol 1998; 9(2): 153-160.)), a Hospital Anxiety and Depression Scale-Depression Subscale (HADS-D) Questionnaire and a Hyperacusis (Geräuschuberempfindlichkeit-Fragebogen (GÜF)) Questionnaire (if applicable).

Visit 2 (baseline): The subject is asked about adverse events and changes in concomitant medication/disease, which events/changes are documented. The subject is evaluated for study eligibility based on a review of the inclusion/ exclusion criteria. Trial procedures as well as allowed and forbidden concomitant medications are reviewed with the subject. An initial Tinnitus Interview is conducted. The subject also completes a THF-12, HADS-D Questionnaire and GÜF Questionnaire (if applicable). The subject is enrolled in the study and study medication (placebo or neramexane) is dispensed as described below.

Visit 3 (Week 4): This visit occurs at the end of the 4-week up-titration sequence. The subject is asked about adverse events and changes in concomitant medication/disease, which events/changes are documented. A follow-up Tinnitus Interview is conducted. The subject also completes a THF-12, HADS-D Questionnaire and GÜF Questionnaire (if applicable). Medication compliance is assessed, and medication for the next 4 weeks is dispensed as described below.

Visit 4 (Week 8): This visit occurs at the end of the first 4-week fixed-dose double-blind treatment period. The subject is asked about adverse events and changes in concomitant medication/disease, which changes are documented. Blood samples are collected in order to determine neramexane pre-dose concentration. A follow-up Tinnitus Interview is conducted. The subject also completes a THF-12, HADS-D Questionnaire and GÜF Questionnaire (if applicable). Medication compliance was assessed and, medication for the next 4 weeks is dispensed as described below.

Visit 5 (Week 12): This visit occurs at the end of the second 4-week fixed-dose double-blind treatment period. The subject is asked about adverse events and changes in concomitant medication/disease, which changes are documented. A follow-up Tinnitus Interview is conducted. The subject also completes a THF-12, HADS-D Questionnaire and GÜF Questionnaire (if applicable). Medication compliance is assessed and, medication for the next 4 weeks is dispensed as described below.

Visit 6 (Week 16, end of treatment). This visit occurs at the end of the 12-week fixed-dose double-blind treatment period. The subject is asked about adverse events and changes in concomitant medication/disease, which changes are documented. A clinical laboratory evaluation is performed. A follow-up Tinnitus Interview is conducted, and the subject completed a THF-12, HADS-D Questionnaire and GÜF Questionnaire (if applicable). Pure-tone audiometry (air conduction) is also conducted.

Visit 7 (Week 20): This visit occurs at the end of the 4-week follow-up period after the last study medication dose. Review of concomitant medications as well as the occurrence of adverse events since the last visit is conducted with subject. A follow-up Tinnitus Interview is conducted, and the subject completes a THF-12, HADS-D Questionnaire and GÜF Questionnaire (if applicable).

Administration of Neramexane

Neramexane mesylate modified release tablets (12.5 mg, 25 mg, 37.5 mg, 50 mg, and 75 mg) and matching placebo tablets are administered for once daily administration.

Medication is supplied in blister boxes that are dispensed from Visit 2 to Visit 5. Each blister box contains 4 blister cards for 4 treatment weeks and 1 blister card as reserve. Blister cards are identified by treatment weeks. Daily medication within the blister cards are identified per day.

Study medication is dispensed at Visit 2 (baseline, day 0). Each patient receives one blister box containing 5 blister cards (including one reserve blister) of double-blind study medication. The dosing regimen is shown in Table 9.

TABLE 9

Administration of Neramexane Mesylate

| Treatment group | Double-blind period Week | | | | |
|---|---|---|---|---|---|
| | 1 | 2 | 3 | 4 | 5-16 (12 weeks) |
| Neramexane 50 mg | 12.5 | 25 | 37.5 | 50 | 50 |
| Neramexane 75 mg* | 12.5 | 25 | 37.5 | 50 | 75 |
| Placebo | 0/0 | 0/0 | 0/0 | 0/0 | 0/0 |

Efficacy

Primary Outcome

The change in THF-12 total score from baseline (Visit 2) to the endpoint visit (Visit 6, i.e. Week 16) is the primary efficacy endpoint in this study.

Secondary Outcomes

THF-12 total score (values and absolute change from baseline) at all post-baseline visits except the endpoint visit.

Change in the THF-12 total score from Week 16 to Week 20 (values and absolute changes).

THF-12 factorial scores (values and absolute change from baseline, including the change from Week 16 to Week 20) at all post-baseline visits.

Hyperacusis questionnaire GÜF ("Geräuschüberempfindlichkeits-Fragebogen"), values and absolute change from baseline, including the change from Week 16 to Week 20, total and factorial scores at all post-baseline visits if hyperacusis is present.

Clinical global impression of change: item 27 of the tinnitus follow-up interview is summarized after dichotomization of the responses in any improvement (values 1, 2, 3) versus no improvement (values 4, 5, 6, 7) and in marked improvement (values 1, 2) versus no marked improvement (values 3, 4, 5, 6, 7).

Total score of HADS-D as well as the depression and anxiety subscale scores (values and absolute change from baseline, also the change from week 16 to week 20) at all post-baseline visits.

Values of tinnitus interview (initial and follow-up) at all post-baseline visits; absolute change from baseline and change from Week 16 to Week 20 for items 8, 9, 10, 19, 20, 21, 24, 25 and 26 of the follow-up interview.

Data Analysis

All efficacy analyses are performed on the ITT population using the last-observation-carried-forward (LOCF) approach. For sensitivity purposes an analysis of the per-protocol set and of observed cases is performed additionally. All statistical tests used for testing the primary efficacy (confirmatory testing) and secondary efficacy criteria (exploratory), and all other statistical tests used for exploratory analyses are two-sided hypothesis tests performed at the 5% significance level. For all variables standard descriptive statistics are calculated.

Change from baseline (Visit 2) to Week 15 in THF-12 total score is analyzed using a two-way ANCOVA model with treatment group and study centers as factors and baseline THF-12 total score as covariate.

For secondary efficacy parameters, the comparison between neramexane and placebo is performed, if appropriate, by visit using a two-way ANCOVA with treatment group and study center as factors and the corresponding baseline value of the efficacy parameter as covariate.

This clinical study demonstrates promising results in terms of efficacy and safety.

Example 3

Double Blind Placebo Controlled Pilot Trial of Neramexane for Treatment of Hearing Loss The objective of this pilot project is to conduct a clinical trial to assess the efficacy of neramexane as a treatment for hearing loss. Patients afflicted with various degrees of hearing loss being treated with neramexane may be expected to demonstrate an improvement in primary (e.g., change to baseline in hearing threshold level) and secondary (e.g., change to baseline in different frequencies on a pure tone audiogram) outcomes as compared to placebo treated patients. A hearing threshold level may be defined as the average of the pure tone hearing threshold levels at testing frequencies of 0.25, 0.5, 1, 2 and 4 kHz.

Study Design

The primary objective of this study is to investigate the safety and efficacy of neramexane mesylate at daily doses of up to 75 mg in the treatment of hearing loss in comparison to placebo.

Administration of Neramexane

Neramexane mesylate 25 mg modified release tablets and matching placebo tablets are administered as film coated tablets.

Neramexane mesylate (or placebo) is uptitrated to a maximum daily dose of 75 mg, starting with a daily dose of 25 mg for one week, and increasing dosage in 25 mg steps at weekly intervals.

Treatment is started in the evening of study day 1. The daily starting dose is 25 mg neramexane mesylate per dose to be taken for 7 days at bedtime. At day 8, the daily neramexane mesylate dose is increased to 50 mg for another 7 days (two tablets in the evening for one week). At day 15, patients are uptitrated to 75 mg neramexane mesylate. Patients continue to take neramexane for 13 weeks (three tablets once daily in the evening for 13). Patients who do not tolerate 75 mg per day may reduce the neramexane mesylate dose by 25 mg to 50 mg for the remainder of the total scheduled treatment duration. For example, patients who do not tolerate a 75 mg dose are allowed to step back to a 50 mg dose. Patients are then asked to stay on the 50 mg dose for the remainder of the total scheduled treatment duration of 7 weeks. This dosing regimen is shown in Table 10.

TABLE 10

Administration of Neramexane mesylate

| Treatment group | 2-week double-blind uptitration period | | 14-week fixed-dose double-blind period | 4-week follow-up |
|---|---|---|---|---|
| | 1 | 2 | 3-16 | 17-20 |
| Neramexane mesylate | 0/25 | 0/50 | 0/75 mg/d | — |
| Placebo | 0/0 | 0/0 | 0/0 | — |

Efficacy

Primary Outcome

Change from baseline in hearing threshold level of left/right ear (dB) calculated as average of the pure tone hearing level threshold levels at 0.25, 0.5, 1, 2 and 4 kHz.

Secondary Outcomes

Change from baseline in high frequency hearing threshold of left/right ear (dB) calculated as average of the pure tone hearing threshold levels at 4, 6, 8 and 10 kHz Change from baseline in individual frequencies (hearing thresholds) on a pure tone audiogram (air conduction)

Number of Responder

Patient-reported outcome on a 11-point Likert-Scale (0=hearing is not a problem, 10=hearing is a problem as much as possible)

Change in hearing impairment based on the hearing threshold level:

| no frequency hearing loss | <20 dB |
|---|---|
| mild hearing loss | 20-40 dB |
| moderate hearing loss | >40-70 dB |
| severe hearing loss | >70-95 dB |
| profound hearing loss | >95 dB |

Data Analysis

All efficacy analyses are performed on the ITT population using the last-observation-carried-forward (LOCF) approach. For sensitivity purposes an analysis of the per-protocol set and of observed cases is performed additionally. All statistical tests used for testing the primary efficacy (confirmatory testing) and secondary efficacy criteria (exploratory), and all other statistical tests used for exploratory analyses are two-sided hypothesis tests performed at the 5% significance level. For all variables standard descriptive statistics are calculated.

Change from baseline (Visit 2) to Week 16 in the hearing threshold level of left/right ear (dB) calculated as average of the pure tone hearing level thresholds at 0.25, 0.5, 1, 2 and 4 kHz are analyzed using a two-way ANCOVA model with treatment group and study centers as factors and baseline hearing threshold as covariate.

For secondary efficacy parameters, the comparison between neramexane and placebo is performed, if appropriate, by visit using a two-way ANCOVA with treatment group and study center as factors and the corresponding baseline value of the efficacy parameter as covariate.

The neramexane treated group demonstrates an improvement in primary outcome as well as secondary outcomes as compared to the placebo group.

Titration packages included within the scope of the present invention will be better understood in connection with the following examples, which are intended as an illustration of and not a limitation upon the scope of the invention.

Example 4

The titration package shown in FIGS. 1-4 comprises, two physically separate entities, in the following referred to as "cover" and "insert". The cover is not shown in the Figure. The outside cover may be a sleeve that slides over the insert (1) and essentially fits therewith, i.e. the outer dimensions of the insert as folded are essentially the same as the inner dimensions of the cover. The insert (1) may also be presented without a cover.

Figure 3:
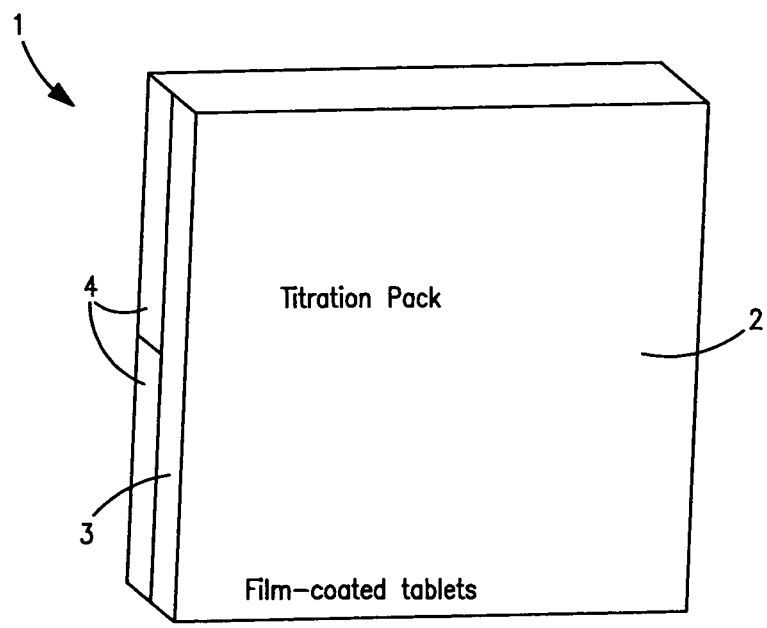
Figure 4:
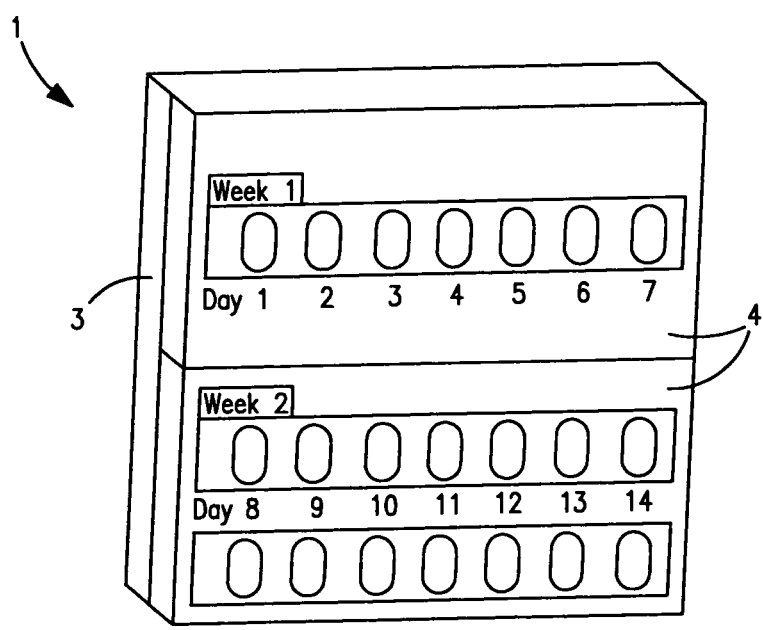

If a cover is used, the insert (1) is (completely) contained inside the cover when the insert is completely folded and the titration package is properly closed (see FIG. 3).

In the closed stage, a kit comprising the package and the dosage forms in differing doses may further comprise instructions on a separate leaflet, wherein the leaflet is slipped in the space between cover and insert. The leaflet may also be (partly) attached to either the insert (1) or the cover.

As shown in FIG. 1, the insert (1) consists of a flat central area (2) in the shape of a "square". Four rectangular areas (in the following referred to as "flaps") (3) and (4) are attached to the four outer edges of said central flat area. The square may be made of a plasticized cardboard material. The square as such comprises no further parts, in particular no blister cavities. Product information may be imprinted onto this area.

Figure 2:
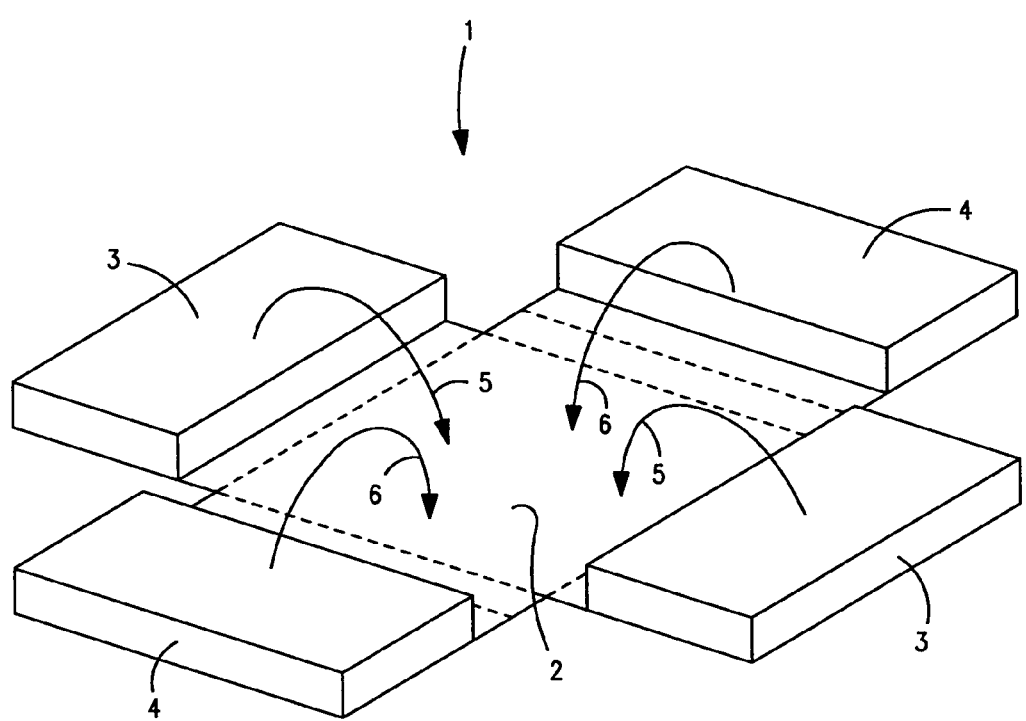

In the completely unfolded state of the insert (1) as shown in FIGS. 1 and 2, the four flaps (3) and (4) are attached to the square (2) and extend along the length of each of the four outer sides (edges) of the square. The flaps are may be made of a double layer of the same material as the square. The flaps comprise the blister cavities for holding the dosage forms as described in more detail below.

All flaps (3), (4) can be folded along a first pre-folded edge (being the above-mentioned outer edge of the square). Two Opposing flaps (4) comprise a second edge inside the flap area that is also pre-folded. This staggering of the distances between the edges of the two sets of opposite flaps allows to fold the flaps while accommodating the blisters that typically have a thickness of several mm (see FIG. 2). As shown in FIG. 2, flaps (3) are folded in first in movement (5) while flaps (4) are folded on top of flaps (3) in movement (6). Once folded, the flaps lie perpendicular to each other, one set of two (4) on top of the other set of two (3), thus completely covering the center square (2) without protruding the same (see FIGS. 3 and 4).

One flap comprises one "row" or "column" and the remaining flaps comprise two "rows" or "columns" (which line(s) of blisters is seen as a "row" and which is seen as a "column" depends on how the insert is oriented) of more than two, for example seven, blister cavities, respectively (see FIG. 1).

In the unfolded stage (FIGS. 1 and 2) of the insert, the "rows" and "columns" are not in contact with each other and are clearly separated from each other.

The insert may be labeled as follows: the flap containing one row/column of seven blisters comprises one label printed onto each flap indicating the number of the week (i.e., "Week 1"), and the remaining flaps which contain two rows/columns of seven blisters each comprise one label printed onto each flap indicating the number of the week (i.e., "Week 2" to "Week 4").

Consecutive weeks may be arranged on adjacent flaps (i.e., the flap of "Week 1" is immediately adjacent to the flaps of "Week 2" and "Week 4", while "Week 3" is located opposite on the other side of the square).

Alternatively, consecutive weeks are arranged in pairs opposite to each other (i.e. the flap of "Week 1" is immediately adjacent to the flaps of "Week 3" and "Week 4", respectively, while "Week 2" is located opposite on the other side of the square).

Each row(s) of blisters (one week) may be positioned on a background bar that is colored, wherein the coloring may be a darker shade of grey/blue the higher the dose (i.e. grey for Week 1 and dark blue for Week 4). Each flap may also comprise one set of seven indicia ranging from day "1" to "28" next to each blister to indicate successive days of the four weeks. In particular, one flap may have blisters labeled "Day 1, 2, 3, 4, 5, 6, 7", the next flap may have blisters labeled "Day 8, 9, 10, 11, 12, 13, 14" and so on (see FIG. 1). The aforedescribed labeling may be present on the inner and on the outer side of the flap (see FIGS. 1 and 4).

The outside of each flap may also be labeled in the lower left corner of the outside of each flap with a value for the respective dose of the 1-amino-alkylcyclohexane (e.g., neramexane mesylate).

Example 5

Figure 5:
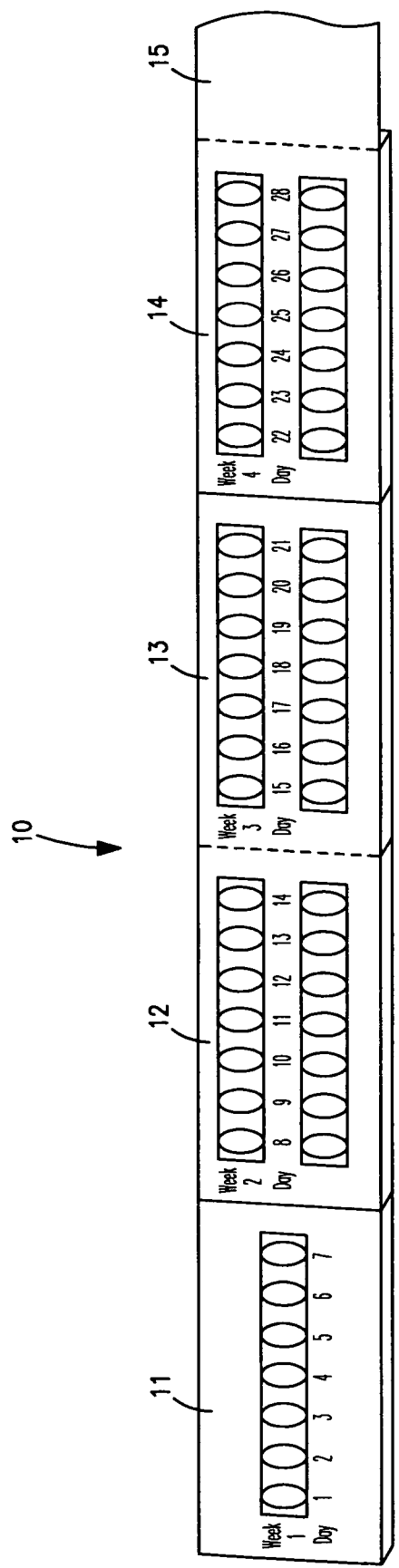
FIGS. 5-6 show the titration package described in Example 4.
Figure 6:
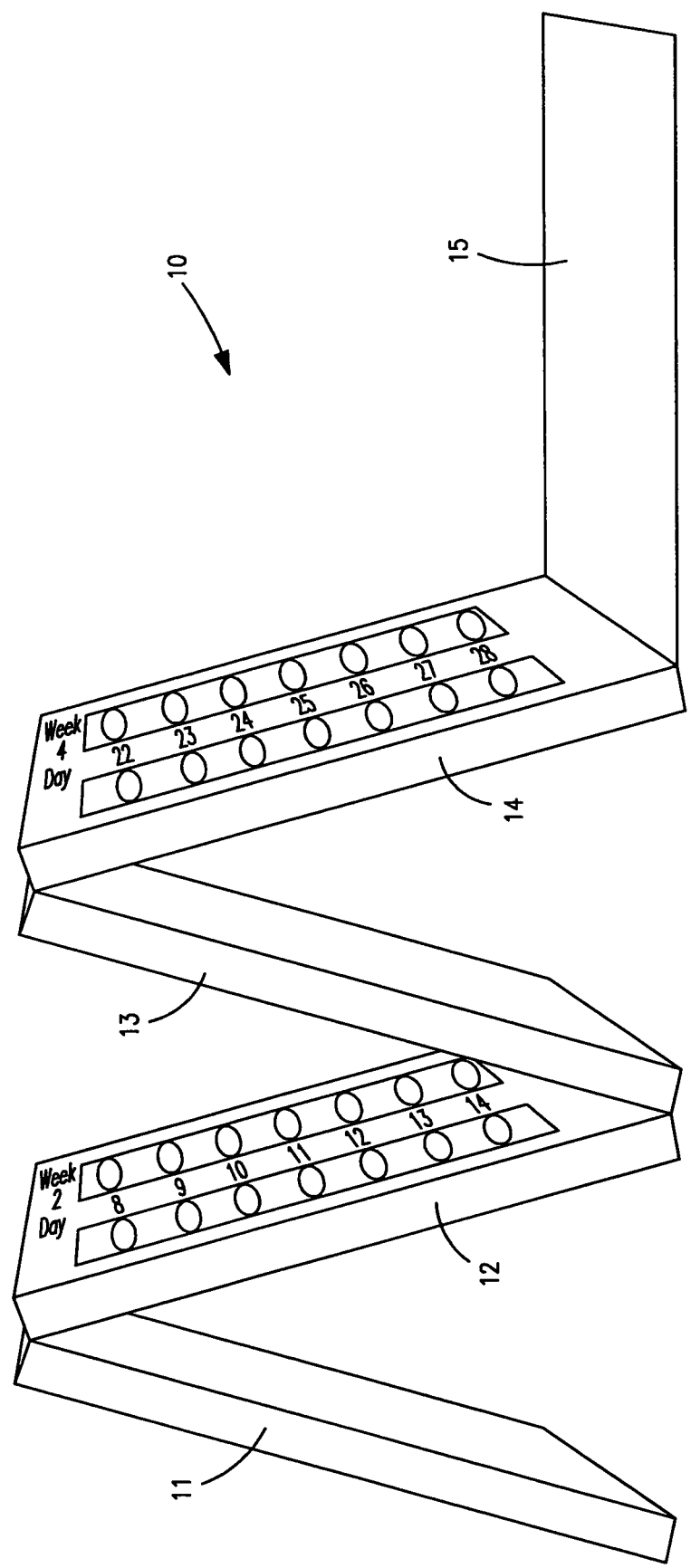

The titration package shown in FIGS. 5 and 6 comprises an insert (10) essentially consists of a "train" of two or more (e.g., four) foldable compartments (11)-(14), i.e. rectangular boxes comprising, in this case, seven or fourteen blister cavities per box. The compartments are connected by hinge-type joints (15), for example made of a flexible paper-like material.

The compartments/boxes (11) to (14) of the train have dimensions comparable to the flaps (3) and (4) discussed in the previous example.

The four compartments (boxes) form a "train" of compartments, i.e. the first compartment is foldably connected to the second compartment, the second compartment is foldably connected to the third compartment and the third compartment is foldably connected to the fourth compartment (see FIGS. 5 and 6).

In the fully extended state (FIG. 5), the four compartments are lying flush next to each other.

In the fully folded state, the four boxes/compartments are lying one on top of the other forming a rectangular box of the same length and width as the individual compartment.

In an intermediate stage, due to the flexible connection ("hinge") between two adjacent compartments, the four boxes/compartments form the shape of an "M" in various degrees of compression or extension (see FIG. 6). Optionally, attached leaflet (15) may provide relevant information.

Each compartment may be labeled to show the week (ranging from "Week 1" to "Week 4"), the dose, and the day of the week.

Furthermore, the increasing dosage between the sets may be indicated by a background coloring bar underlining the seven blisters, the intensity of which increases from the leftmost ("Week 1") compartment to the rightmost compartment ("Week 4").

Example 6

Figure 7:
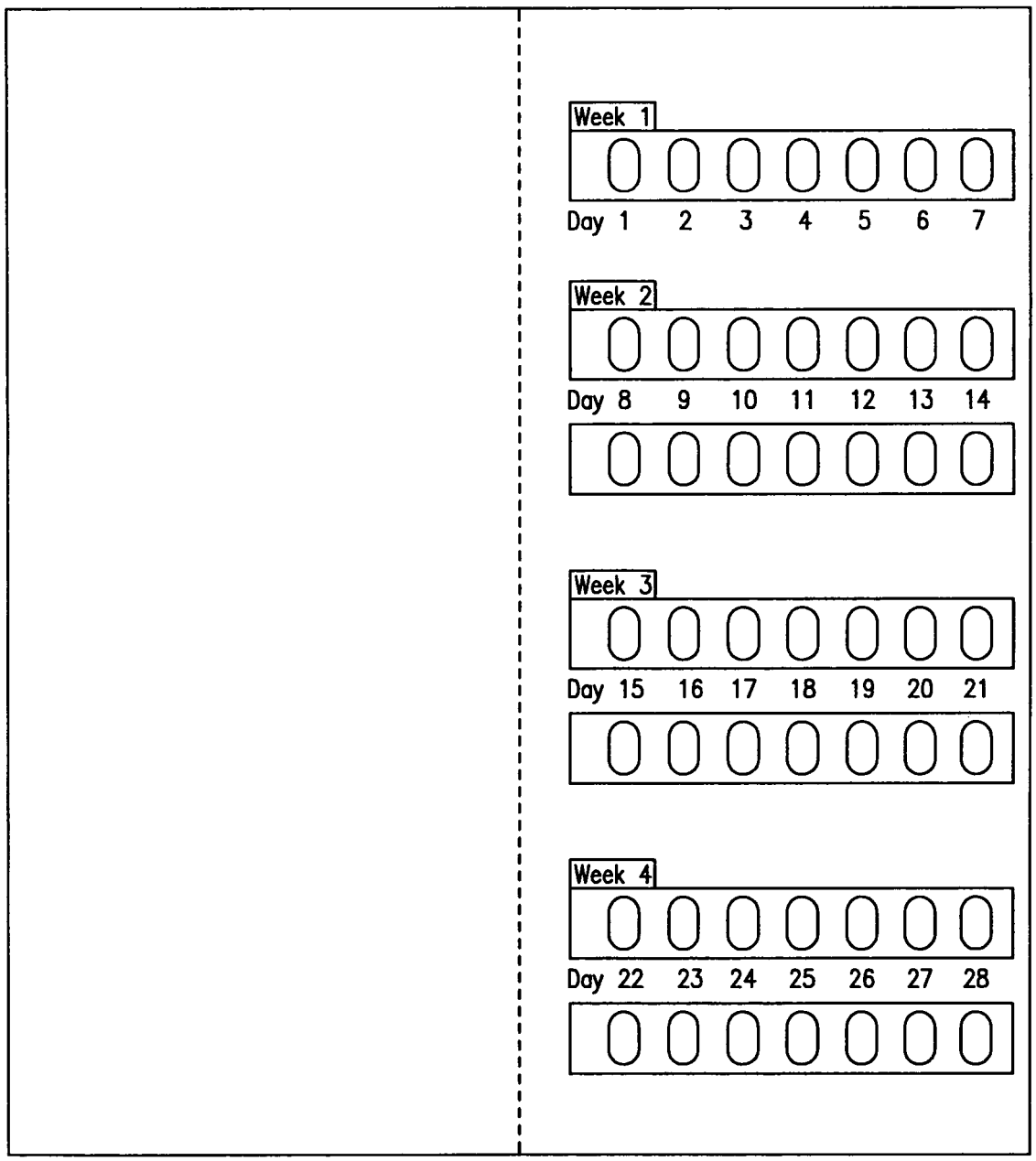
FIG. 7 shows the titration package described in Example 5.

The titration package shown in FIG. 7 comprises a rectangular backing which is divided into four sections. Each section is comprised of seven (in one row) or fourteen blister (in two rows of seven) cavities.

Each section be labeled to show the week (ranging from "Week 1" to "Week 4"), the dose, and the day of the week.

Example 7

Figures 8, 9:
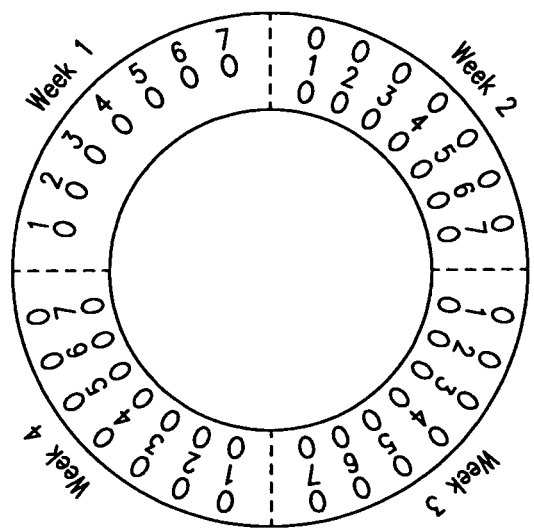
FIG. 8 shows the titration package described in Example 6.
FIG. 9 shows the titration package described in Example 7.

The titration package shown in FIG. 8 comprises a circular backing which is divided into four sections. Each section is comprised of seven (in one row) or fourteen blister (in two rows of seven) cavities.

Each section be labeled to show the week (ranging from "Week 1" to "Week 4"), the dose, and the day of the week.

Example 8

The titration package shown in FIG. 9 comprises a foldable backing made of, for example, a flexible paper-like material, which is divided into four compartments. The first compartment is foldably connected to the second compartment, the second compartment is foldably connected to the third compartment and the third compartment is foldably connected to the fourth compartment.

Each compartment is comprised of seven (in one row) or fourteen blister (in two rows of seven) cavities.

Each compartment may be labeled to show the week (ranging from "Week 1" to "Week 4"), the dose, and the day of the week.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference.

The invention claimed is:

1. A method of treating tinnitus, in a subject in need thereof, comprising administration of a therapeutically effective amount of a 1-amino-alkylcyclohexane derivative selected from neramexane and pharmaceutically acceptable salts thereof, wherein the 1-amino-alkylcyclohexane derivative is administered in a titration scheme comprising up titration of the 1-amino-alkylcyclohexane derivative in increasing dosages of 25 mg or 12.5 mg steps at weekly intervals over a period of four weeks to achieve a body weight-adjusted target dose of 50 mg/day for patients with a body weight of up to 90 kg, or over a period of five weeks to achieve a body weight-adjusted target dose of 75 mg/day for patients with a body weight of equal to or greater than 90 kg.

2. The method of claim 1, wherein the titration scheme comprises up-titration of neramexane, or a pharmaceutically acceptable salt thereof, over a period of four weeks to achieve an effective dose of 50 mg per day.

3. The method of claim 1, wherein neramexane or a pharmaceutically acceptable salt thereof is administered according to the following schedule: once daily at a dose of 12.5 mg per day for the first week, twice daily, wherein each dose is 12.5 mg for the second week, twice daily, wherein one dose is 12.5 mg and the other dose is 25 mg for the third week, and twice daily, wherein each dose is 25 mg for the fourth week.

4. The method of claim 1, wherein the titration scheme comprises up-titration of neramexane, or a pharmaceutically acceptable salt thereof, over a period of five weeks to achieve an effective dose of 75 mg per day.

5. The method of claim 1, wherein neramexane or a pharmaceutically acceptable salt thereof is administered according to the following schedule: once daily at a dose of 12.5 mg per day for the first week, twice daily, wherein each dose is 12.5 mg for the second week, twice daily, wherein one dose is 12.5 mg and the other dose is 25 mg for the third week, and twice daily, wherein each dose is 25 mg for the fourth week, and twice daily, wherein each dose is 37.5 mg for the fifth week.

6. The method of claim 3, wherein in weeks during which mixed doses are administered, the dose comprising the higher concentration is administered in the second daily dose.

7. The method of claim 5, wherein in weeks during which mixed doses are administered, the dose comprising the higher concentration is administered in the second daily dose.

8. The method of claim 1, wherein neramexane is administered as its mesylate salt.

* * * * *

UNITED STATES PATENT AND TRADEMARK OFFICE
CERTIFICATE OF CORRECTION

| | |
|---|---|
| PATENT NO. | : 8,877,814 B2 |
| APPLICATION NO. | : 12/733645 |
| DATED | : November 4, 2014 |
| INVENTOR(S) | : Barbara Ellers-Lenz et al. |

It is certified that error appears in the above-identified patent and that said Letters Patent is hereby corrected as shown below:

Title Page

Item (75) Inventor Address for Hagen Kruger: "Frankfurt am Main" should be -- Hamburg --.

In the Claims

Column 31, Claim 1, Line 19 and 20: "up titration" should be -- up-titration --.

Signed and Sealed this
Nineteenth Day of May, 2015

Michelle K. Lee
*Director of the United States Patent and Trademark Office*